US012224047B2

(12) United States Patent
Velichkovich et al.

(10) Patent No.: US 12,224,047 B2
(45) Date of Patent: Feb. 11, 2025

(54) SYSTEMS AND METHODS OF RADIOLOGY REPORT PROCESSING AND DISPLAY

(71) Applicant: Virtual Radiologic Corporation, Minneapolis, MN (US)

(72) Inventors: Zeljko Velichkovich, Carver, MN (US); Theodore J. Walker, Kansas City, MO (US); Patrick T McGaughey, Chanhassen, MN (US); Shwan Kim, Thousand Oaks, CA (US); Kimberley S. Miller, Mount Vernon, WA (US); Timothy Braatz, Waverly, PA (US)

(73) Assignee: Virtual Radiologic Corporation, Minneapolis, MN (US)

( * ) Notice: Subject to any disclaimer, the term of this patent is extended or adjusted under 35 U.S.C. 154(b) by 88 days.

(21) Appl. No.: 17/900,736

(22) Filed: Aug. 31, 2022

(65) Prior Publication Data

US 2024/0071586 A1    Feb. 29, 2024

(51) Int. Cl.
*G16H 15/00*    (2018.01)
*G06F 40/20*    (2020.01)
*G16H 50/70*    (2018.01)

(52) U.S. Cl.
CPC .............. *G16H 15/00* (2018.01); *G06F 40/20* (2020.01); *G16H 50/70* (2018.01)

(58) Field of Classification Search
CPC ......... G16H 15/00; G16H 50/70; G06F 40/20
See application file for complete search history.

(56) References Cited

U.S. PATENT DOCUMENTS

2012/0221347 A1    8/2012  Reiner
2014/0149407 A1    5/2014  Qian et al.
(Continued)

FOREIGN PATENT DOCUMENTS

WO    2013160382    10/2013
WO    2021233795    11/2021

OTHER PUBLICATIONS

Goff, Daniel J, "Automated Radiology Report Summarization Using an Open-Source Natural Language Processing Pipeline", J Digit Imaging, 31(2), (2018), 185-192.
(Continued)

*Primary Examiner* — Chinyere Mpamugo
(74) *Attorney, Agent, or Firm* — Schwegman Lundberg & Woessner, P.A.

(57) ABSTRACT

Systems and methods for identifying and presenting prior findings data in a radiology review workflow, based on natural language processing (NLP) of unstructured radiology report text, are disclosed. In an example, prior findings are generated with operations including: receiving text from a prior radiology report prepared for a patient in a prior radiology study; processing the text with a trained NLP engine to classify discrete prior findings in the prior radiology study that identify observed condition(s) and characteristics of the observed condition(s); and outputting or presenting the prior findings, such as in a radiology review user interface. In an example, the radiology review user interface displays the observed condition(s) and the characteristic(s) of the observed condition(s) to a user (e.g., a radiologist), and can apply sorting, filtering, or grouping based on pathology phrases or attribute words associated with the observed conditions or the characteristics of such observed conditions.

25 Claims, 14 Drawing Sheets

(56) References Cited

U.S. PATENT DOCUMENTS

| | | |
|---|---|---|
| 2014/0297269 A1 | 10/2014 | Qian et al. |
| 2014/0379378 A1 | 12/2014 | Cohen-solal et al. |
| 2016/0147946 A1 | 5/2016 | Von Reden |
| 2016/0267226 A1 | 9/2016 | Xu et al. |
| 2016/0292392 A1 | 10/2016 | Xu et al. |
| 2016/0364862 A1 | 12/2016 | Reicher et al. |
| 2020/0126648 A1 | 4/2020 | Schadewaldt et al. |
| 2021/0134465 A1 | 5/2021 | Gooßen et al. |
| 2022/0130554 A1* | 4/2022 | Hayter, II .............. G16H 50/70 |

OTHER PUBLICATIONS

Yuan, Jianbo, "Classification of Pulmonary Nodular Findings based on Characterization of Change using Radiology Reports", AMIA Summits on Translational Science Proceedings, (2019), 285-294.

Zhang, Yuhao, "Learning to Summarize Radiology Findings", author preprint, Stanford University, (2018), 10 pgs.

* cited by examiner

| | PHRASE | PATHOLOGY GROUP ▲ | ANATOMY |
|---|---|---|---|
| | | | |
| 🔍 | CHOLECYSTECTOMY (8) | SURGICAL CHANGES | GALLBLADDER |
| 🔍 | COLON RESECTION | SURGICAL CHANGES | COLON |
| 🔍 | HEMICOLECTOMY (7) | SURGICAL CHANGES | COLON |
| 🔍 | COLON CARCINOMA | TUMOR - MALIGNANT OR INDETERMINATE | COLON |
| 🔍 | MASS | TUMOR - MALIGNANT OR INDETERMINATE | |
| 🔍 | METASTASIS | TUMOR - MALIGNANT OR INDETERMINATE | SMALL BOWEL |
| 🔍 | METASTATIC | TUMOR - MALIGNANT OR INDETERMINATE | |
| 🔍 | NODULE (3) | TUMOR - BENIGN | THYROID |
| 🔍 | NODULE | TUMOR - BENIGN | THYROID LOBE |
| 🔍 | NODULE | TUMOR - BENIGN | UPPER LOBE |
| 🔍 | PULMONARY NODULE (2) | TUMOR - BENIGN | LUNG |

SUMMARIZED PRIOR FINDINGS
NOTE: THIS SUMMARY MAY NOT REFLECT ALL FINDINGS IN THE PATIENT'S PRIOR REPORTS.

*FIG. 6A*

SUMMARIZED PRIOR FINDINGS

NOTE: THIS SUMMARY MAY NOT REFLECT ALL FINDINGS IN THE PATIENT'S PRIOR REPORTS.

| EXAM DATA | PHRASE | PATHOLOGY GROUP ▲ | ANATOMY | PARAGRAPH |
|---|---|---|---|---|
| | | ⊟ SURGICAL CHANGES | | |
| 9/15/2018 | CHOLECYSTECTOMY | SURGICAL CHANGES | GALLBLADDER | ORGANS: RIGHT UPPER QUA... |
| 7/23/2019 | CHOLECYSTECTOMY | SURGICAL CHANGES | GALLBLADDER | 67 YEARS OLD, MALE; CONDI... |
| 7/23/2019 | CHOLECYSTECTOMY | SURGICAL CHANGES | GALLBLADDER | GALLBLADDER AND BILE DUCT... |
| 7/23/2019 | CHOLECYSTECTOMY | SURGICAL CHANGES | GALLBLADDER | ENLARGED PROSTATE CORREL... |
| 10/16/2020 | CHOLECYSTECTOMY | SURGICAL CHANGES | GALLBLADDER | GALLBLADDER AND BILE DUCT... |
| 12/30/2021 | CHOLECYSTECTOMY | SURGICAL CHANGES | GALLBLADDER | ORGANS: POST CHOLECYSTES... |
| 12/31/2021 | CHOLECYSTECTOMY | SURGICAL CHANGES | GALLBLADDER | 1. THERE HAS BEEN A CHOL... |
| 12/31/2021 | CHOLECYSTECTOMY | SURGICAL CHANGES | GALLBLADDER | GALLBLADDER AND BILE DUCT... |
| 7/23/2019 | COLON RESECTION | SURGICAL CHANGES | COLON | 67 YEARS OLD, MALE; CONDI... |
| 10/5/2018 | HEMICOLECTOMY | SURGICAL CHANGES | COLON | 1. INTERVAL POSTOPERATIVE... |
| 10/5/2018 | HEMICOLECTOMY | SURGICAL CHANGES | COLON | THERE IS GASTRIC WALL: THICK... |
| 7/23/2019 | HEMICOLECTOMY | SURGICAL CHANGES | COLON | STOMACH AND BOWEL: THE... |
| 7/23/2019 | HEMICOLECTOMY | SURGICAL CHANGES | COLON | ENLARGED PROSTATE CORREL... |
| 1/13/2020 | HEMICOLECTOMY | SURGICAL CHANGES | COLON | 1. RIGHT HEMICOLECTOMY... |
| 1/13/2020 | HEMICOLECTOMY | SURGICAL CHANGES | COLON | HULL THICKENING FUNDUS A... |
| 11/1/2021 | HEMICOLECTOMY | SURGICAL CHANGES | COLON | STOMACH APPEARS NORMAL... |
| | | ⊟ TUMOR - MALIGNANT... | | |
| 3/6/2018 | COLON CARCINOMA | TUMOR - MALIGNANT... | COLON | THERE IS CONCENTRIC MURA... |
| 10/5/2018 | MASS | TUMOR - MALIGNANT... | | TRACHEAL AIRWAY IS PATENT... |
| 10/5/2018 | METASTASIS | TUMOR - MALIGNANT... | SMALL BOWEL | 2. FLUID FILLED DILATED LOO... |
| 10/16/2020 | METASTATIC | TUMOR - MALIGNANT... | | 1. NO NEW EVIDENCE MET... |

*FIG. 6B*

SYSTEMS AND METHODS OF RADIOLOGY REPORT PROCESSING AND DISPLAY

TECHNICAL FIELD

Embodiments pertain to techniques and systems for processing electronic data obtained from (or associated with) diagnostic and evaluative medical procedures. Some embodiments relate to data processing mechanisms for radiology report data, to provide enhanced displays and identification of radiology report information in radiology image interpretation and similar medical settings.

BACKGROUND

The evaluation or interpretation of medical images by a radiologist (commonly referred to as a "radiology read") often involves review of newly captured medical images and a comparison of such images to the information in prior radiology evaluations (commonly referred to as "prior findings"). Typically, a radiologist would review prior findings by browsing previous radiology reports and then opening and reading those reports to find relevant anatomy and conditions. Prior findings in a radiology report are often contained in unstructured text documents, produced from a radiologist narration or notation. As a result, when reviewing prior findings, a radiologist typically will often need to read through the report text to identify relevant prior findings and medical condition states.

In many radiology interpretation interfaces, historical radiology reports are presented in a newest to oldest fashion, allowing the radiologist to review a list of reports, including reports from studies that may or may not be relevant to the current evaluation. A radiologist would then need to open and read each report to find the prior findings and related information that is relevant to the current evaluation. Although technology has been applied to assist radiologists in tasks such as dictating and writing new reports, many aspects of radiology review remain manual and rely on human assessment and skill. The expanding amount of medical data being captured for patients—including from radiology imaging procedures—has led to various delays and challenges to identify and use relevant medical history data.

BRIEF DESCRIPTION OF THE DRAWINGS

FIGS. 6A and 6B illustrate user interface displays providing an output of summarized findings for pathology information from radiology reports, according to an example.

DETAILED DESCRIPTION

Figure 1:
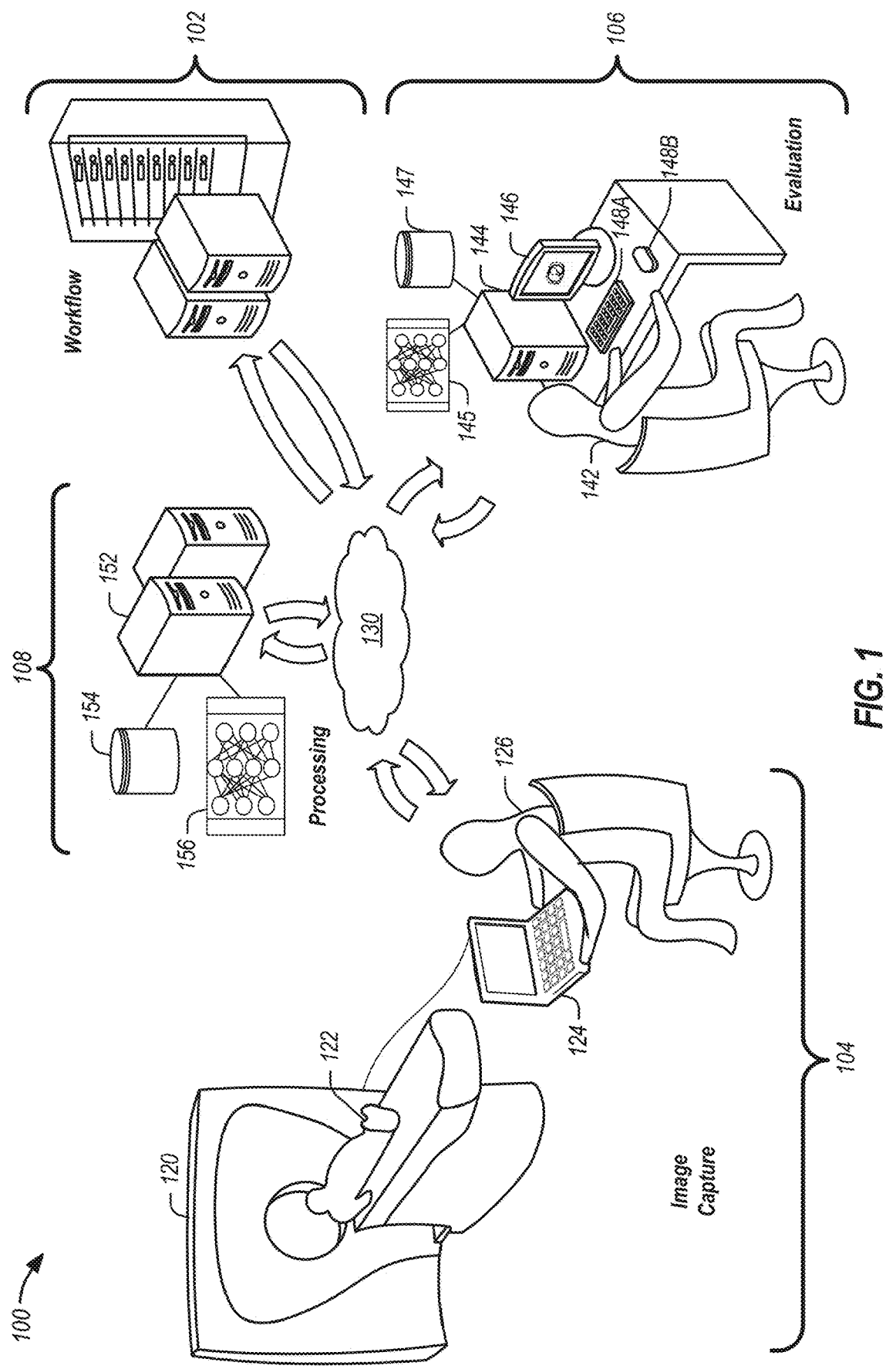
FIG. 1 illustrates a system configuration enabled for capturing, processing, and evaluating medical imaging data in connection with radiology reporting enhancements, according to an example.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations for the analysis and presentation of radiology data and other related medical data. For example, during radiology image evaluation (a radiology "read" or "study"), a variety of data will be considered by a radiologist or other medical professional to make or confirm a diagnosis. The data considered by the radiologist may include a radiology order or clinical notes relating to the current patient condition, as well as historical data from the current patient.

For many patients with chronic conditions or a complicated medical history, their historical data may span a long range of time and involve multiple prior radiology studies. The contents of such historical data may include image and text data, including images and reports performed on the patient for the same, related, or different medical conditions. The presently disclosed systems and methods provide technical advances for identifying, finding, displaying, and interacting with "prior findings" from such data.

With conventional systems, a number of additional actions are performed to find and review data when a radiologist attempts to compare a current radiology study with a prior radiology study. In examples discussed below, a patient medical history "summarization tool" is established to assist a radiologist to navigate such historical data. In one aspect, the summarization tool operates to automatically identify anatomical features, conditions, measurements, and the like from the historical data. Such information may be grouped or indexed based on a medical condition or topic, and accompanied by functionality such as sorting and filtering. Such information may also be automatically presented, or integrated into review aspects of a radiology read workflow. Accordingly, instead of having a radiologist having to manually read and search for relevant keywords or concepts in different reports, such information may be automatically identified and presented to a radiologist to ease the navigation and search burden (and, to more quickly and accurately identify relevant information).

In these and other configurations, various technical features are extended to assist in solving technical problems involving information retrieval and data processing. A first set of technical features includes the use of a natural language processing (NLP) engine, which allows prior text reports, summaries, narrations, tags, keywords, etc. to be analyzed. In an example, a NLP engine is specially trained to provide an understanding of particular pathology or anatomical features, to allow identification of the meaning of different phrases and keywords. The natural language processing engine also may be extended to recognize whether particular conditions or pathologies are negative or positive (e.g., are indicated or not indicated by images), to identify a measurement of some anatomical feature (e.g., the size or shape indicated by the images), or to extract other meaning or data values from other forms of text or metadata. Thus, the operation and output of an NLP engine may be customized for handling specific forms of radiology data.

A second set of technical features is described to perform data analysis and information classification based on particular anatomical/pathological considerations, such as by body part/area or specific pathology. Such information may be used to help produce classifications or related categorizations of particular anatomical features, states, or diagnoses, which is useful in settings where multiple terms, words, or phrases are used to represent the same or related medical condition. Additionally, it will be understood that such classifications or categorizations by pathology can enable a number of subsequent display functions and features (e.g., highlighting, sorting, filtering, grouping).

A third set of technical features is described to allow the output or presentation of such historical data, in new formats and with new forms of functionality. Different user interface tools are described to build on the NLP features and classification features discussed above, to assist radiology review workflows and procedures. This may be followed by procedures that validate user-input data when crafting a report for the current exam, such as to validate or verify the outcome of a newly drafted radiology report against prior findings (e.g., to flag or check findings that are inconsistent with past reports).

These configurations and processes may be implemented by electronic (e.g., computer-implemented) operations in specialized software, including in user interfaces provided by radiology viewing systems and equipment. Related configurations and processes may also be implemented by client and server computers, network communications, and related processing and data evaluation functions. Thus, although the present techniques are described with reference to medical evaluative and diagnostic settings such as radiology interpretations, a variety of technical issues are addressed with the following examples including with information retrieval, searching, data normalization, user interactivity, and display outputs, and associated improvements to technical systems used in these settings.

In some of the following examples, reference is made to specific radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a qualified (e.g., licensed and credentialed) radiologist. It will be understood that the applicability of the presently described techniques and systems will extend to a wide variety of imaging data and healthcare data representations produced by—or as a result of—various medical procedures and specialties, including those not involving radiology imaging modalities or radiology professionals. Other specialties which may provide evaluative data include, but are not limited, to pathology, medical photography, medical data measurements such as electroencephalography (EEG) and electrocardiography (EKG) procedures, cardiology data, neuroscience data, dental and dentistry imaging, preclinical imaging, and other data collection procedures occurring in connection with telemedicine, telepathology, remote diagnostics, and other applications of medical procedures and medical science. Accordingly, the data indexing, searching, organizing, classification, normalization, and display techniques discussed herein may apply to a variety of medical data types, settings, and use cases, including other types of reports, images, and multi-image (e.g., video) representations and visualizations.

FIG. 1 provides an illustration of an example medical imaging system configuration 100 (e.g., a radiology imaging arrangement), which provides data for medical imaging procedures to be analyzed with the examples described herein. The medical imaging system configuration 100 may be used for capturing medical image data in one location and for reviewing medical images associated with the data in another location. The medical imaging system configuration 100 may include many geographically separated imaging devices and many image review terminals, not shown. The medical imaging system configuration 100, in a radiology setting, may be embodied as a remote teleradiology system connected to a plurality of healthcare locations, as a localized radiology system used in a single hospital, healthcare provider network, or private radiology practice. The medical imaging system configuration 100 may also operate as an information processing network used to process data from respective imaging procedures regardless of the location of an eventual imaging evaluation.

For purposes of illustration, the medical imaging system configuration 100 depicted in FIG. 1 includes an image capture system 104, a workflow processing system 102, an image evaluation system 106, and a data processing system 108. The image capture system 104, for example, may include an imaging device 120, such as a CT scanner, a MRI scanner, or another imaging system (e.g., a radiology imaging modality). Using an energy source such as x-rays or magnetic fields, for example, the imaging device 120 may capture image data associated with a subject 122 (e.g., a patient). It will be understood that many other networks, systems, devices, entities, and actors are not depicted but may be involved in the medical imaging system configuration 100 and aspects of imaging, processing, workflow, or evaluation operations.

In an example, the imaging device 120 is controlled by a technologist 126 at the medical facility through the use of a workstation terminal or other electronic input control 124. Prior to the technologist 126 conducting the imaging procedure for a patient, information may be entered into or synchronized with the electronic input control 124. Information from an electronic medical record (EMR) or healthcare information system (HIS) may also be accessed or updated for the imaging procedure. Relevant information and metadata for the imaging procedure may be placed within the image data itself, or hosted within another data store for further access and processing. For example, the imaging device 120 may produce radiological images generally consistent with the Digital Imaging and Communications in Medicine (DICOM) format, other industry-accepted standards, or proprietary standards.

Consistent with the appropriate image format, the images produced by the image data source may include or be linked to metadata. This metadata may be generated by the imaging device 120, from input collected by the electronic input control 124, or from input from a HIS or EMR. Further, a series of images produced by the image data source may be obtained directly by the imaging device 120 in the facility shown in FIG. 1, or may be transferred in whole or in part from another image capturing device connected to the imaging device 120 or the medical facility's local network. The imaging data source may also include data transmitted through use of a local (e.g., on-premises) imaging server (not shown), such as a DICOM server or other Picture Archiving and Communication System (PACS). The metadata within each imaging data file may include identification information such as a patient identifier and an identifier of the series of images, in addition to information about the type of imaging modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images, with the collection of some identifiable series of images typically referred to as a "study." In some implementations, the image data may be used to produce a three-dimensional model that can be further manipulated and reformatted for generating two-dimensional (or three-dimensional) images. In other implementations, the image data may include three-dimensional models, visualizations, or graphical data generated by the imaging device 120 or intermediate processing systems. Image data captured by the imaging device 120 may be stored and processed by the workflow processing system 102 or another local or remote imaging device server (e.g., one or more computers with a processor and a memory), and may be provided to other systems and computers in the medical imaging system configuration 100 through network 130 (e.g., an intranet or the Internet).

In various examples, medical imaging procedure data provided to the workflow processing system 102 results in data being stored, processed, and communicated among one or more computers. For example, the workflow processing system 102 may determine that the medical imaging procedure data is to be forwarded to a particular computer associated with an evaluating user 142 (e.g., a radiologist workstation) at an image evaluation system 106. As shown, image data may be provided or directed by the workflow processing system 102 through the network 130 to the image evaluation system 106. Additionally, the medical imaging procedure data provided to the workflow processing system 102 results in the image data or related medical data being processed by the data processing system 108. This medical imaging procedure data may be processed by the data processing system 108 prior to, in parallel with, or at the same time as the provision or assignment of the image data to the image evaluation system 106. The data processing system 108 may assist actions taken at the image capture system 104, the workflow processing system 102, or the image evaluation system 106, through the use of AI and advanced data analytics. The data processing system 108 may utilize AI models and algorithms, among other rules or processes, to perform various aspects of data validation, recognition, classification, inferences, regression, prediction, or analysis. Such AI models and algorithms may include the NLP processing techniques discussed in more detail below.

The image evaluation system 106, for example, may include an image display system 144 (e.g., one or more computers with a processor and a memory), a display device 146 (e.g., a monitor), and input devices 148A, 148B (e.g., keyboards, computer mice, joysticks, touch interfaces, voice recognition interfaces, and the like). In some implementations, image data may be processed by the image display system 144 and visually presented to the evaluating user 142 as one or more images or visualizations at the display device 146. Using the input devices 148A-148B, the evaluating user 142 may interact with the presented images or visualizations, for example, by manipulating one or more user controls included in a graphical user interface presented at the display device 146 in association with the images or visualizations.

For example, the evaluating user 142 may view an image, a series of related images, or one or more visualization generated from an image, and may specify one or more adjustments, such as zooming, panning, rotating, changing contrast, changing color, changing view angle, changing view depth, changing rendering or reconstruction technique, and the like. By viewing and interacting with presented image data and with the user interface, for example, the evaluating user 142 may indicate, select, confirm, or input a diagnostic finding value related to a radiological imaging procedure performed on the subject 122. The image evaluation system 106 also may utilize a processing algorithm 145, including from AI models distributed or managed by the data processing system 108, to perform processing on the received study, historical patient data, or other input data 147. Such AI models may include NLP models for analysis of text data from prior radiology reports, discussed herein.

The data processing system 108 may include a data processing server 152 (e.g., one or more computers with a processor and a memory). In some implementations, medical imaging procedure data (or images or individual data representations from such data) may be processed by a compiled binary or other software executed with the processor and the memory of the data processing server 152, to perform specialized image or text processing operations, among other operations. The binary or other software executed with the data processing server 152 may implement one or more AI models (provided by an artificial neural network, convolutional neural network, recurrent neural network, reinforcement learning model, natural language processing model, machine learning algorithm, decision tree, support vector machine, genetic algorithm, etc.) on the medical imaging procedure data from current or prior radiology studies, based on the use of input data 154 and a trained processing algorithm 156.

In some examples, the processing algorithm 156 includes an NLP model algorithm, and the input data 154 includes text data from prior radiology reports, as discussed herein. Various AI data indications may be produced by the data processing server 152 of the data processing system 108 to cause processing and display changes for the subsequent workflows and evaluation activities of the medical imaging procedure data. In various implementations, the data processing server 152 may establish descriptors, markings, annotations, or additional metadata for images of the medical imaging procedure data; in other examples, the data processing server 152 may indicate the presence of particular identified conditions, the absence of certain identified conditions, the likelihood/probability/or other certainty score of such identified conditions, and other related outputs from the operation of a recognition algorithm on the medical imaging procedure data, prior reports, or the like.

Other image or workflow processing actions may occur at the workflow processing system 102 or data processing system 108, based on the AI data indications and historical medical data (including, data from prior findings). Such actions may determine or change the assignment of a particular study to a particular image review system, or the prioritization of a particular study in a worklist within a particular image review system. Likewise, the workflow processing system 102 may perform additional or substitute study assignments, verifications, data transfers, or other processing with the image evaluation system 106 based on a particular medical condition or state identified by the AI model, or metadata associated with the AI model processing (e.g., confidence level).

The data processing system 108 may serve as an orchestrator that selects particular AI models or processing approaches for use and execution, distributes AI processing tasks or models among local and remote settings, ensures accuracy and maintenance of the AI models, and the like. Execution of such AI models is not limited to operations at a single location of the data processing system 108; rather, multiple on-premises servers, edge computing servers, cloud computing servers, and the like (not shown) may be coordinated for processing operations. Additionally, instances of the AI models (such as algorithm 145) may be executed at the image evaluation system 106 including on client computing devices during, before, or after the image evaluation process.

Processing of unstructured text data may be invoked by an NLP engine during, before, or after the image evaluation process to extract prior findings relevant to one or multiple medical conditions. As an example, software implementing an NLP engine may employ one or more models, trained using machine learning technologies, to recognize particular medical conditions (e.g., named pathologies in a radiology report) and medical condition states (e.g., pathology attributes in a radiology report such as size, growth, acuity, etc.). Such software may use the trained models in combination with other software algorithms to categorize the unstructured report text, identify information relevant to the current exam, and provide an interface for sorting, filtering, and reviewing the information.

Figure 2:
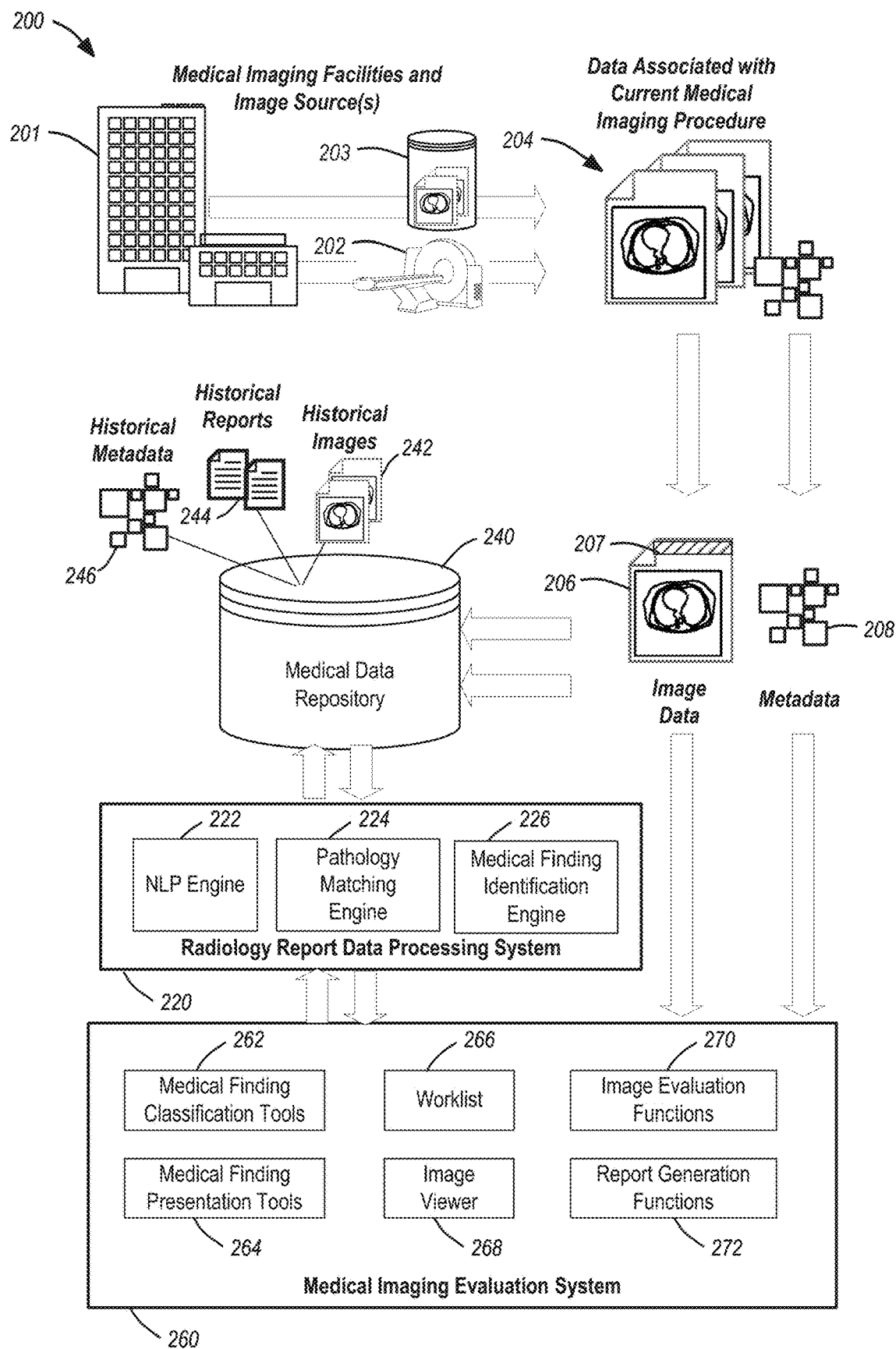
FIG. 2 illustrates system operations for the processing and display of medical imaging and associated radiology report data associated with a medical imaging procedure, according to an example.

FIG. 2 illustrates a system operations diagram 200 of an example workflow for the processing and display of data produced from a particular medical imaging study (e.g., a new radiology study) with use of a radiology report data processing system 220 according to various examples. In any radiology workflow which evaluates a medical condition, it is important to consider the progression of the medical condition. To determine this progression, a radiologist may wish to compare a current set of images with information from at prior images and reports. The conventional way to perform this evaluation, by the review of prior reports, can be time-consuming and error-prone-especially for patients with a long list of prior radiology reports or complicated medical histories.

In the workflow of FIG. 2, a set of processing engines, including an NLP engine 222, a pathology matching engine 224, and a medical finding identification engine 226, use NLP or other algorithms to analyze text and dynamically identify prior findings from historical radiology studies. For instance, the radiology report data processing system 220 can detect and classify particular medical conditions and states (attributes) of the particular medical conditions, based on the text provided in a current or prior radiology report. (e.g., text in historical reports 244 generated from prior radiology studies). Such medical conditions and states then may be used to assist evaluation and review of new radiology images at a medical imaging evaluation system 260, including with the use of medical finding classification tools 262 (e.g., tools to access or identify a classification from the prior medical findings) and medical finding presentation tools 264 (e.g., tools to allow sorting, grouping, searching, or filtering of presentations for the prior medical findings).

In detail, the system operations diagram 200 is depicted as including image data 206 and metadata 208 (e.g., order data) originating from a current (e.g., new) medical imaging procedure, and historical images 242, historical reports 244, and historical metadata 246 from past (e.g., prior) medical imaging procedures of the patient. The image data and metadata 208 may be produced from an imaging modality 202 or obtained from a data store 203 at or associated with one or more medical imaging facilities 201, with the combination of image data and order data collectively referred to as imaging procedure data 204. It will be understood, however, that the imaging procedure data 204 may also be accompanied, integrated, or associated with data from a medical data repository 240, including data originating from medical information systems (e.g., EMR data, HIS data, and the like) that is not necessarily produced from the medical imaging procedure to be evaluated.

The system operations diagram 200 also illustrates functional operations which may implement all or parts of the medical imaging system configuration 100 or specific components of the workflow processing system 102, the evaluation processing system 106, and the data processing system 108. Such functional operations include the receipt and processing of the imaging procedure data 204 (e.g., radiology study data, including one or both of a radiology order and a radiology imaging data) originating from a particular medical imaging facility or imaging source of the medical imaging facilities 201. This imaging procedure data 204 is processed to obtain identifying data associated with the medical imaging procedure, including an identification of imaging characteristics, type of the imaging procedure, and associated information related to the evaluation of the imaging data. For example, the medical imaging procedure data may include image data 206 and image metadata 207, where the image metadata 207 may include identification information such as a patient or study identifier and an identifier of the series of images, in addition to information about the type of imaging modality and the techniques used to obtain the images. The imaging procedure data 204 also may provide other metadata 208 for an associated order to perform the diagnostic evaluation of the image data. For example, the metadata 208 may include data from an HL7 Order Message (ORM) sent when a healthcare provider requests a service, procedure, or treatment for a patient.

The imaging procedure data 204 may be analyzed by other data processing systems (not shown) for the processing of the image data 206, the image metadata 207, or other metadata 208. For example, automated image recognition may analyze the image data with a trained image recognition model (e.g., provided by one or more AI models) with use of a processing algorithm and other condition detection logic (not shown). In some examples, distinct processing algorithms and trained image recognition processing may be used to detect the characteristics (e.g., attributes or properties) of respective medical conditions directly from images. For instance, a model or algorithms may be used to classify, detect, or measure the likelihood of one or multiple of many identifiable medical conditions. Other medical data, such as information from a patient's medical history or records, may be evaluated to further improve the accuracy and operation of a model or processing algorithm, or of a current evaluation.

The radiology report data processing system 220 may be used to classify or generate an indication of one or more medical conditions (and medical condition attributes) from prior findings. Details for these medical conditions may include a confidence level for the presence or absence of certain conditions (e.g., a score or measurement that corresponds to a level of recognition or confidence of whether certain conditions are or are not indicated), identification of specific features or areas in the image in which certain conditions are detected or likely to occur, identification of images or areas of images in the prior study in which certain conditions are detected or likely to occur, and similar identifications and indications.

The NLP engine 222 performs analysis of unstructured text content from prior radiology studies to derive meaning and context of particular textual expressions. In an example, the NLP engine is trained to analyze the text content based on particular patterns, words, or terms commonly used in medical or radiology settings. Also in an example, the NLP engine 222 produces an index (e.g., a searchable or cacheable index) of the incidence of particular words or terms used in particular radiology studies.

The pathology matching engine 224 analyzes the results of the NLP engine 222 to identify the mention of a particular medical condition (a pathology) relating to a particular anatomical area or description. The particular pathologies and attributes of such pathologies may be matched (and, aggregated or normalized) based on the usage of particular pathology phrases. In an example, pathology phrases are a combination of one or more words used by a radiologist to describe a pathology and/or process. In a further example, such pathology phrases are associated with pathology groups or concepts, discussed in more detail below.

The medical finding identification engine 226 may produce an identification of a medical condition state (a pathology attribute) relating to a particular anatomical area or description. Such a finding may be produced from a combination of one or more words used by a radiologist to describe change, growth, acuity, confidence, negation, limitation, characterization, points of reference (location/anatomy), laterality, and/or size. Various logic or rules may be used to identify and extract values of such attributes from prior report text.

Any of the engines 222, 224, 226 may be implemented by features of AI algorithms or trained models. For example, the NLP engine may be a trained AI model embodied by a computer-generated deep convolutional neural network trained by numerous historical studies and expert results, including with the use of supervised learning (e.g., training from a labeled data set) or unsupervised data (e.g., training from an unlabeled data set). The training of such AI models or algorithms may be provided as a result of earlier evaluation actions at the evaluation system 260, or other human created or verified results from prior workflow or training activities.

The evaluation system 260 may provide a number of features in order to enable a radiologist to perform the radiology read of the current medical imaging procedure data 204. The evaluation system 260 may include a worklist 266 of assigned studies to review by a particular evaluating user; an image viewer 268 to output and control the display of various images from the image data; image evaluation functions 270 to assist the user with manual or automated review of the data 204; and report generation functions 272 to assist the radiologist to prepare and compile a diagnostic report (e.g., a new radiology report) for medical findings from the data 204.

The evaluation system 260 also includes features that integrate the use of information extracted from prior findings. These features include medical finding classification tools 262 which assist with the identification of particular medical conditions from prior findings (or, from current findings). These features also include medical finding presentation tools 264 which assist with the presentation of prior findings (or, current findings) during the review of images from a current radiology study, or during the preparation of a radiology report or similar data entry.

In an example, the presentation of the prior findings may be filtered to include only those relevant to the current study by default (e.g., because not all prior findings are relevant to the current radiology study). A default setting may be to filter pathology groups and anatomies from prior findings to only those that are related to the current imaging study. For instance, a prior finding of a finger fracture should not be shown as a relevant prior finding if the current exam undergoing evaluation is an ultrasound imaging of a pregnancy.

The presentation of the prior findings may also provide other display features to allow a radiologist to sort, group, or refine display of the prior findings. Such a display may be sorted: based on an evaluated importance of a type of prior finding (e.g., cancers, surgical changes); based on anatomy; based on pathology or diagnosis; and the like. The presentation tools may also include navigation features to offer the ability to quickly view a finding within the context of the full prior report (e.g., a link to the relevant prior radiology report).

Other aspects of the prior findings may be used to assist the evaluation or comparison of medical images from current or prior studies. These may include modifications to the order, orientation, hanging, or positioning of particular images, series, or comparison studies (for example, to quickly indicate, highlight, or display images depicting significant prior findings). Such modifications may be implemented in a display or graphical user interface automatically, or in response to user selection (e.g., in response to alerts or user-selectable options in a graphical user interface that can quickly implement modifications and suggested actions).

Although not expressly depicted within FIG. 2, other data flows may be established or updated between the radiology report data processing system 220 and other components of the evaluation system 260. Additionally, the operations performed in connection within FIG. 2 may be implemented with not-shown features of a PACS or RIS, features of a HIS or data informatics system, or other components of a medical image procedure management system.

The display of a timeline or sortable list of prior radiology pathologies for a particular patient is merely one example of a radiology read workflow that is assisted by the automated identification of prior findings. Other example use cases for prior findings in a radiology read workflow may include: performing a manual search for pathology or pathology attributes in specific anatomical areas; generating one or more notifications to a radiologist if current report dictation is contradictory with findings in a previous report; identification of recurring pathology trends that may indicate particular medical conditions, or outcomes such as abuse or other cases of non-accidental trauma; automatically prompting a radiologist to comment on previously identified findings that require follow-up evaluation; and the like. Thus, it will be understood that a variety of actions may be initiated or triggered during (or after) a radiology read workflow based on the identification of prior findings.

Figure 3A:
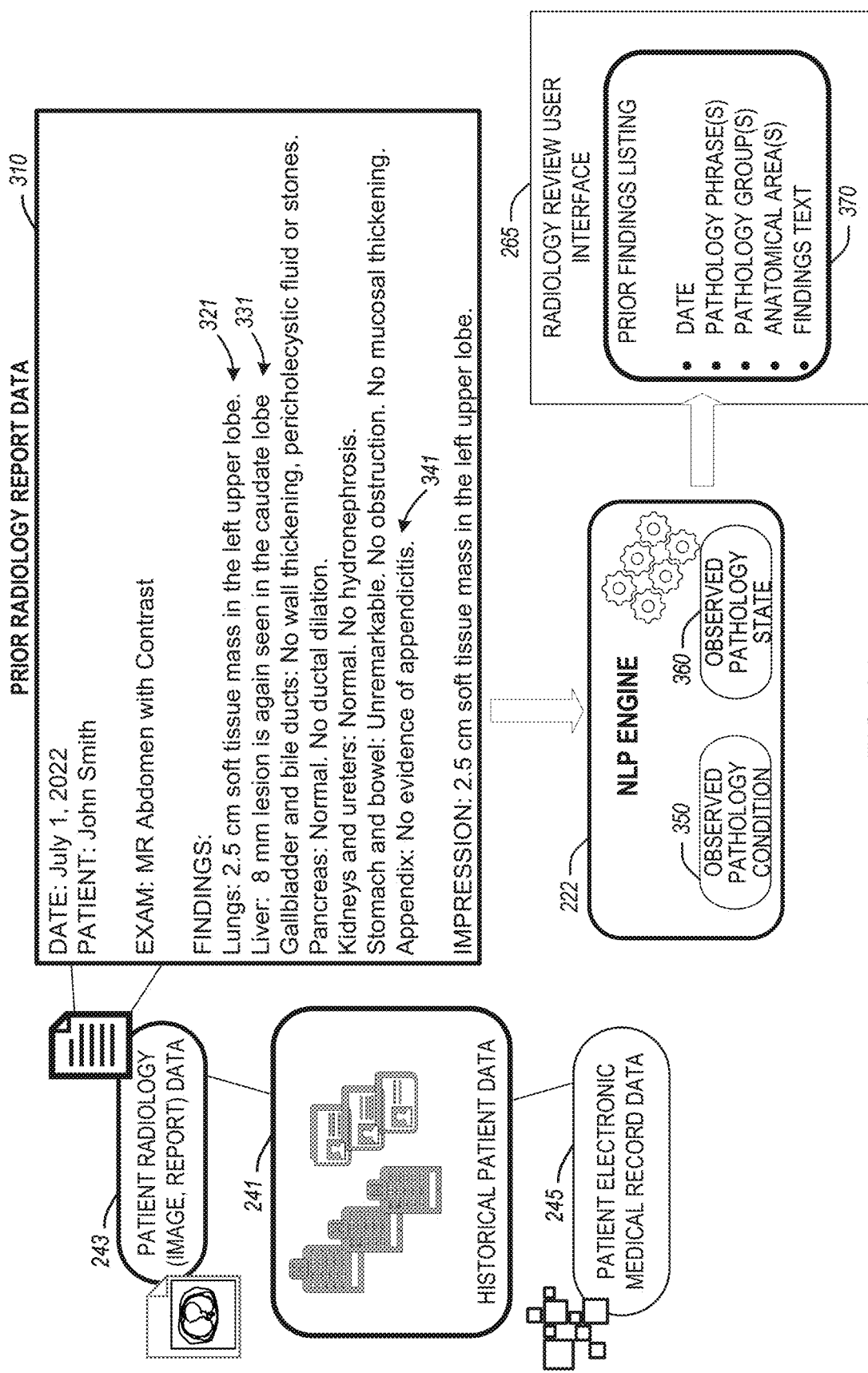
FIGS. 3A to 3D illustrates a diagram of unstructured report data processing with a radiology report data processing system, according to an example.

FIG. 3A illustrates a diagram of unstructured report data processing with a radiology report data processing system, according to an example, such as with use of the NLP engine 222 from the radiology report data processing system 220. Building on the example of FIG. 2, this diagram depicts how historical patient data 241 (e.g., maintained in the repository 240) provides patient radiology data 243 (e.g., images and reports) and patient electronic medical record data 245 (e.g., EMR data or metadata). At the core of the patient radiology data 243 are a series of one or more radiology reports (e.g., historical reports 244), each of which includes a text description of the radiology read (e.g., depicted in unstructured text report 310).

The NLP engine 222 may be adapted for semantic processing to match or identify a pathology of particular medical conditions, based on NLP operations to recognize words or terms that are specific to radiology reports or related medical evaluative content. The NLP engine 222 is depicted in FIG. 3A as producing data (e.g., a classification) for an observed pathology condition 350 and an observed pathology state 360, based on the evaluation of the unstructured text 310 from radiology report data.

Figure 3B:
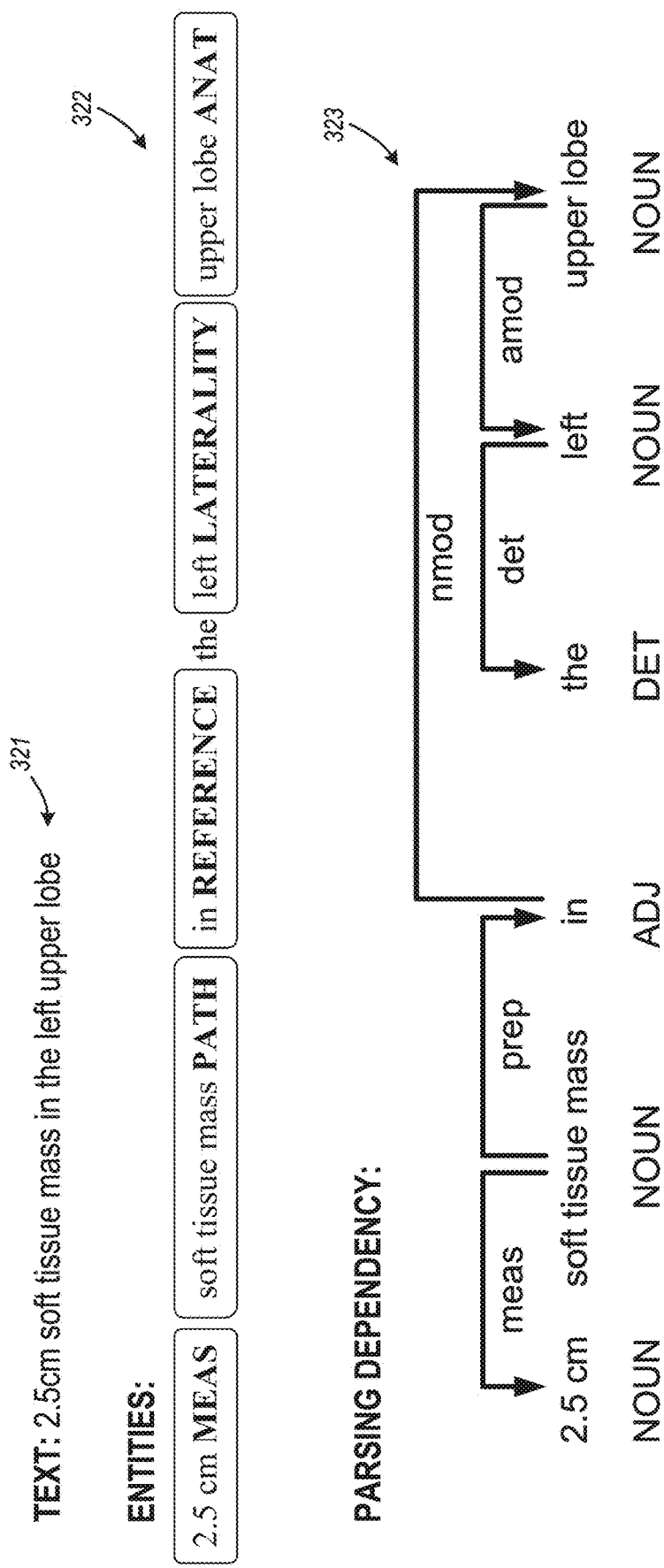

The data produced from the NLP engine 222 may be provided for output in one or more displays, such as in a radiology review user interface 265. In a specific example, illustrated in more detail in FIGS. 6A and 6B, below, a listing of prior findings 370 is produced which can be graphically interacted with by a radiologist. This listing of prior findings 370 may indicate, for each prior finding (e.g., for each identified pathology):

Date of prior finding
Pathology phrase associated with the prior finding
Pathology group associated with the prior finding
Anatomical areas associated with the prior finding
Text of the prior finding FIG. 3B illustrates a further example of unstructured report data processing, specifically showing parsing of the text phrase 321 from report 310: "2.5 cm soft tissue mass in the left upper lobe". Here, a set of entities 322 are extracted from an NLP parsing tree 323. The NLP parsing tree 323 is used to split apart portions of the text sentence, so that the subject of the text (relating to a pathology condition, specifically "soft tissue mass") are related to a set of attributes (e.g., measurement of "2.5 cm", laterality of "left", reference of "in", and anatomy of "upper lobe").

Figure 3C:
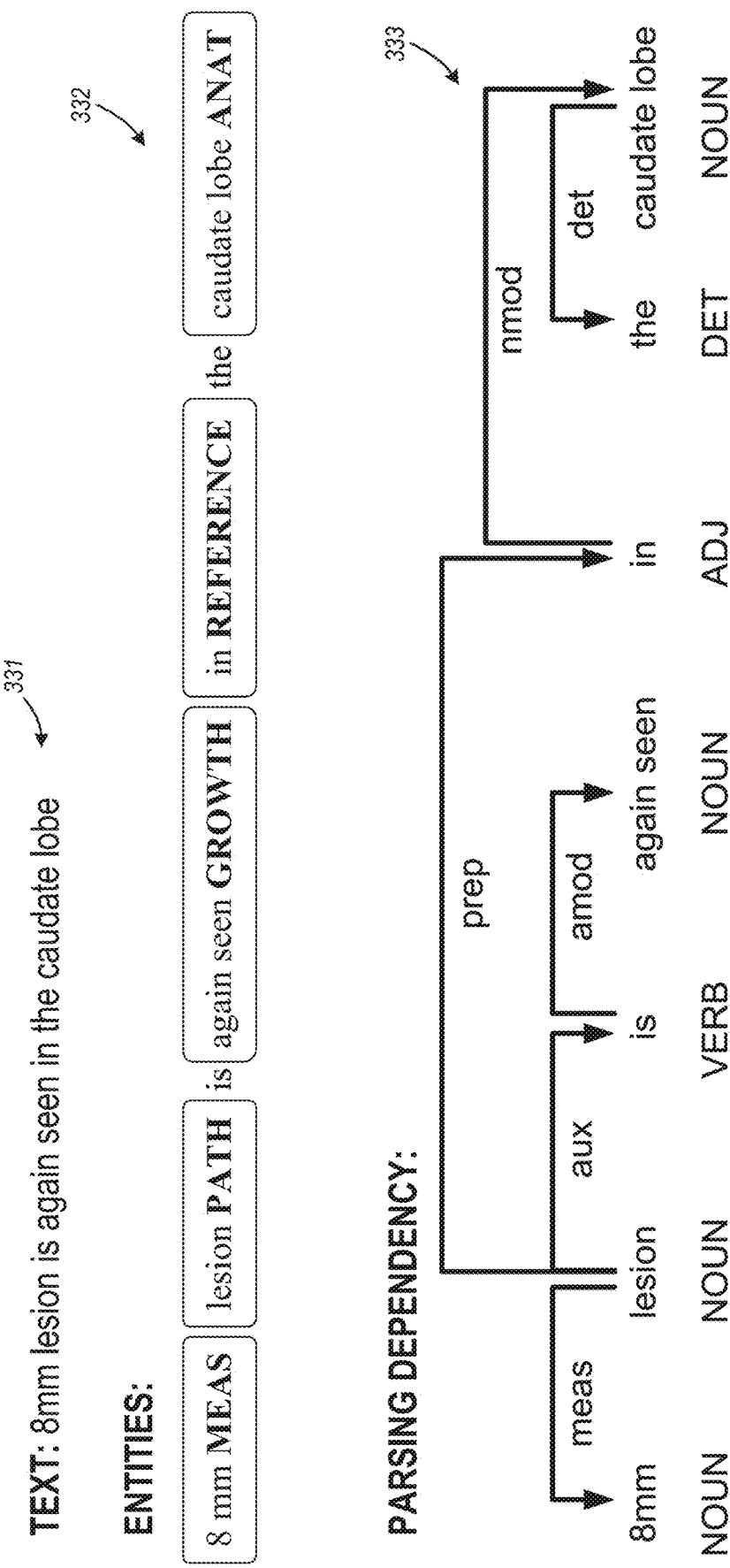

FIG. 3C illustrates another example of unstructured report data processing, specifically showing parsing of the text phrase 331 from report 310: "8 mm lesion is again seen in the caudate lobe". Here, the set of entities 332 are extracted from an NLP parsing tree 333, which shows how subject of the text (another pathology condition, "lesion") are related to another set of attributes (e.g., measurement of "8 mm", growth of "again seen", reference of "in", and anatomy of "caudate lobe").

Figure 3D:
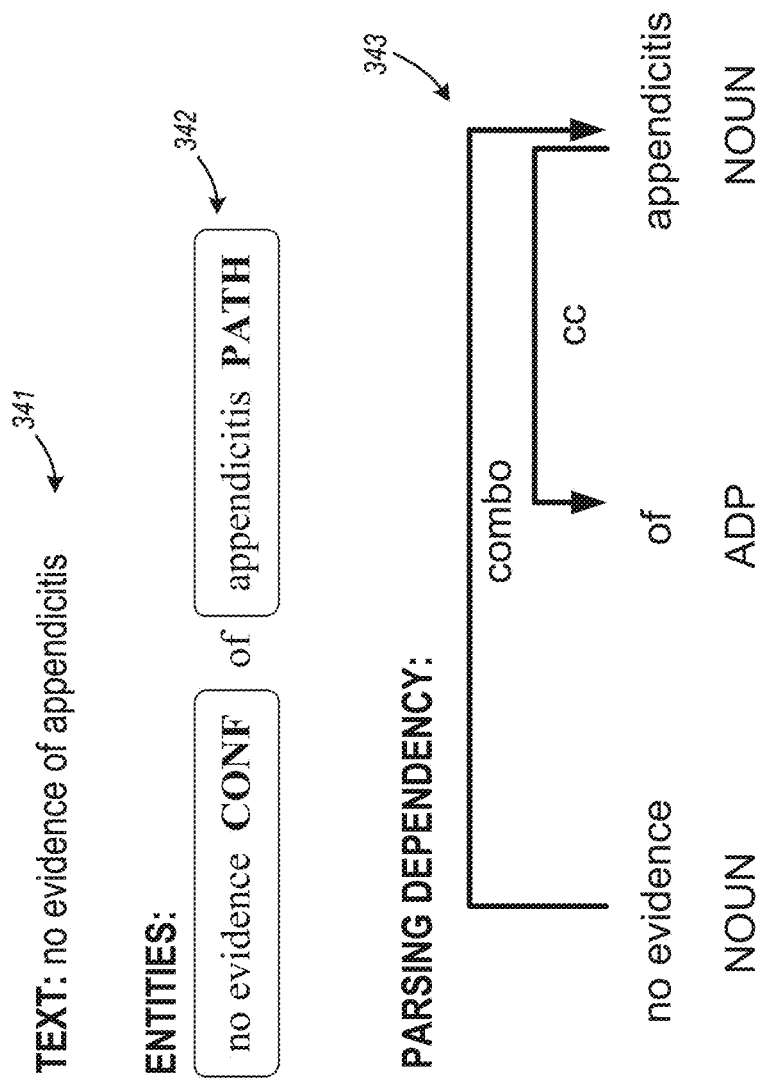

FIG. 3D illustrates another example of unstructured report data processing, specifically showing parsing of the text phrase 341 from report 310: "no evidence of appendicitis". Here, a set of entities 342 are extracted from an NLP parsing tree 343 to show how the subject of the text (another pathology condition, "appendicitis") has another set of attributes (e.g., confidence of "no evidence").

The following table demonstrates a result of parsing the text phrases 321, 331, 341, and other text phrases, to produce data with the following attributes.

TABLE 1

| Sentence | Pathology | Size | Laterality | Anatomy |
|---|---|---|---|---|
| "2.5 cm soft tissue mass in the left upper lobe." | Soft tissue mass | 2.5 cm | Left | Upper lobe |
| "8 mm lesion is again seen in the caudate lobe" | Lesion | 8 mm | | Caudate lobe |
| "No evidence of appendicitis." | Appendicitis | | | |
| "No acute fracture." | Fracture | | | |

| Sentence | Pathology | Confidence | Growth | Negated |
|---|---|---|---|---|
| "2.5 cm soft tissue mass in the left upper lobe." | Soft tissue mass | | | |
| "8 mm lesion is again seen in the caudate lobe" | Lesion | | Again seen | |
| "No evidence of appendicitis." | Appendicitis | No evidence | | |
| "No acute fracture." | Fracture | | | True |

The attributes depicted in TABLE 1 and in FIGS. 3B-3D are for purposes of illustration only. It will be understood that other attributes and categorizations can also be used as a result of NLP processing and prior finding classifications.

Figure 4:
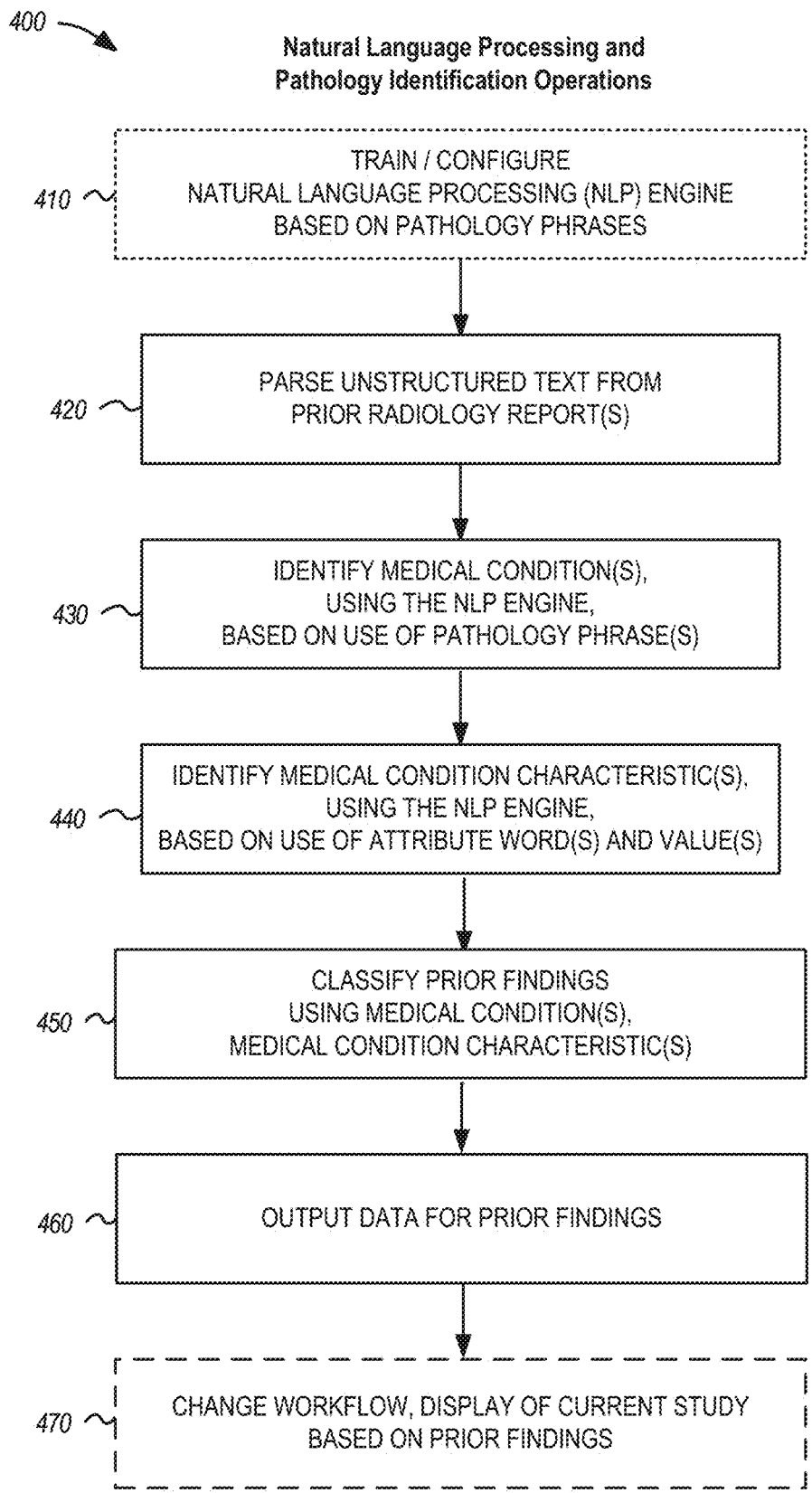
FIG. 4 illustrates a flowchart of operations performed with a natural language processing engine for analysis of radiology report data, according to an example.

FIG. 4 illustrates a flowchart 400 of operations performed with a natural language processing engine for analysis of radiology report. Such operations may be implemented at a processing system (e.g., at the data processing system 108, or at the workflow processing system 102), but other implementation examples may also apply.

The example flowchart 400 may be used for implementing the prior finding identification features discussed in FIGS. 1 to 3, or the use cases further discussed below. In particular, the flowchart 400 details the use of natural language processing on unstructured text from a prior radiology report. It will be understood, however, that such natural language processing and pathology identification may be extended to other types and forms of data (e.g., electronic medical record data).

In operation 410, an NLP engine is trained or configured based on pathology phrases. Such training may occur at a prior time, and include the use of pathology phrases extracted or labeled from radiology reports, medical dictionaries, and the like.

At operation 420, unstructured text from one or more prior radiology reports for a particular patient is parsed by the NLP engine. Multiple training vectors and targets may be identified to assist the identification of particular textual phrases used by radiologists and other medical professionals.

At operation 430, one or more medical conditions are identified for the particular patient, using the NLP engine. In an example, such conditions are identified based on the use of pathology phrases (e.g., a combination of one or more words used by radiologist to describe a pathology and/or process) appearing in the radiology report.

In operation 440, one or more medical condition characteristics (also referred to herein as "attributes") are identified. In an example, such characteristics are identified based on the use of one or more particular attribute words in the radiology report, which indicate one or more values. In an example, such attributes are provided from a combination of one or more words used by a radiologist to describe change, growth, acuity, confidence, negation, limitation, characterization, points of reference (e.g., referencing location/anatomy), laterality, and/or size.

In operation 450, prior findings from prior radiology reports are classified using the medical conditions and medical condition characteristics (e.g., from operations 430, 440). In some examples, such classification includes the use of specific groupings referred to as "pathology groups", which encompasses pathology phrases. Examples of pathology groups include, but are not limited to. Cancer; Surgical Changes; Masses and Nodules; Cystic Lesions; and the like. In further examples, pathology attributes (e.g., negation and anatomy attributes) may further influence which pathology phrases are associated with a particular pathology group.

In operation 460, data for the prior findings is output. The medical conditions and medical condition characteristics (and, accompanying pathology phrases, attributes, or groups) may be used to provide one or more displays of patient-specific data and simplified outputs of data. Such displays may be customized or modified based on the type of prior findings, number of prior findings, and the like. Other data outputs of prior findings may also be provided, such as in the form of a timeline, summary, etc.

In operation 470, which may be optionally implemented automatically (or, which may be optionally implemented by manual or user interactions), various aspects of a radiology imaging evaluation may be changed. Such changes may include a change to a radiology workflow or a change to a radiology imaging display, based on the contents of the prior findings. Further aspects of display operations are discussed in the flowchart of FIG. 5.

Figure 5:
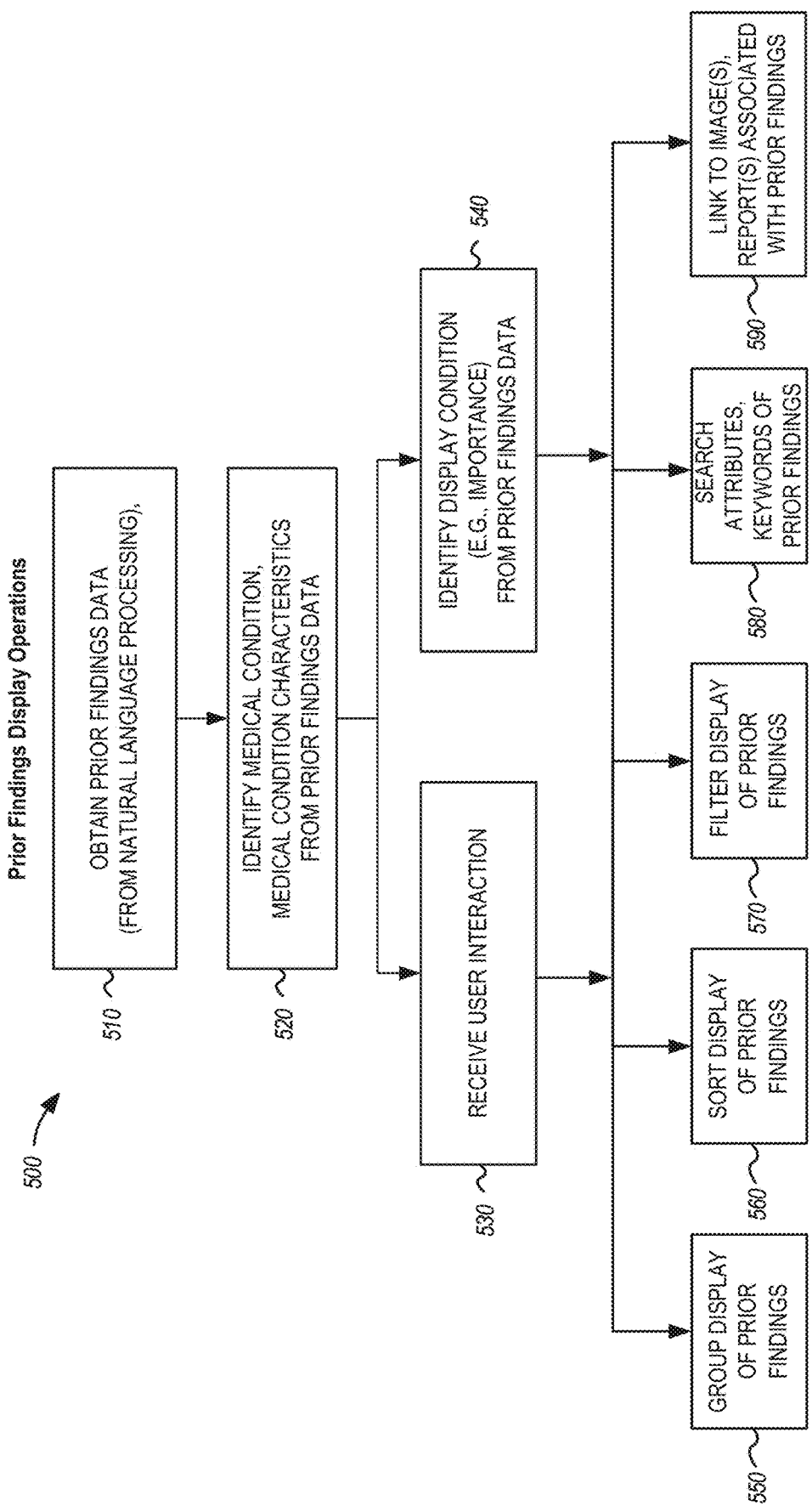
FIG. 5 illustrates a flowchart of operations performed for display of prior findings from radiology report data, according to an example.

FIG. 5 illustrates a flowchart 500 of example operations performed for display of prior findings from radiology report data, according to an example. Such operations may be implemented at a radiologist workstation (e.g., at evaluation system 106, or at evaluation system 260), but other implementation examples may also apply.

At operation 510, prior findings data is obtained from the use of NLP analysis and classifications. Such prior findings data may be generated for the patient (and the NLP analysis may be performed) at the same time or immediately before a new radiology study evaluation of the patient, such as when a radiology order is created or processed. Alternatively, such prior findings may be generated for the patient at an earlier time (e.g., days, weeks, or years before). For instance, prior findings data for a patient may be continually logged or cached in a database and updated on an ongoing basis as new radiology studies or medical data is received.

At operation 520, a medical condition and medical condition characteristics are identified from the prior findings data. This may include the identification of particular pathology phrases, pathology attributes, and pathology groups. The identification of a medical condition and medical condition characteristics may also include a determination of related or relevant conditions or properties (e.g., so that only related or relevant prior findings will be displayed, and so non-relevant or unrelated prior findings can be filtered out or not displayed).

Further display adaption, based on prior findings, may be triggered based on the receipt of user interaction (at operation 530) or by other manual action; or, may be automatically triggered based on the identification of a particular display condition (at operation 540), rules, or events. As one example, user interaction at operation 530 may include a selection by a radiologist to expand or reduce displayed information on prior findings. Also as another example, automatic implementation at operation 540 may perform certain actions in the radiology read workflow (e.g., displaying an alert, displaying a certain portion of a report or image, displaying a link to an image or portion of a report associated with a finding, etc.) based on the occurrence of certain prior findings.

Accordingly, display operations may be triggered according to the aspects of operations 510-540. Such display operations may include: a grouping based on prior findings (operation 550) (e.g., as shown in the examples of FIG. 6A and FIG. 6B with the grouping of particular radiology report phrases, pathology groups, and anatomy); a sorting based on prior findings (operation 560) (e.g., as shown in the examples of FIG. 6A and FIG. 6B with the sorting by pathology group); a filtering based on prior findings (operation 570) (e.g., as discussed in the examples above, including to filter the groups and anatomies to those that are related to the current imaging study, or that are specified by a custom filter); a search of attributes, classifications, or keywords based on prior findings (operation 580); a link to one or more images or reports associated with prior findings (operation 590). As will be understood, the list of relevant prior findings may be long, so various functions may be enabled to allow a radiologist to sort and filter by anatomy, pathology, exam date, or specific pathology phrase. Additionally, more than one of these operations 510-540 can be applied one or more times to a set of data, allowing sorting, grouping, and filtering on multiple dimensions of data.

Also in an example, the search of attributes or keywords based on prior findings (operation 580) may enable a search of known (and potentially not displayed) prior findings from an indexed archive. For instance, a radiologist could manually indicate an anatomy of interest (by keyword entry, or an on-screen selection from an anatomical or pathological listing) to identify all historical prior findings related to that anatomy. The results of the search may be further sorted, grouped, and filtered.

FIGS. 6A and 6B illustrate example user interface displays providing an output of summarized findings for pathology information from radiology reports. The display 600A in FIG. 6A provides an initial view of a listing of pathologies detected from prior reports. Specifically, the display 600A includes columns to identify the occurrence of phrases 620, including a display of de-duplicated or consolidated occurrences (to combine/group the occurrence of pathology phrases such as "cholecystectomy", "hemicolectomy", and "nodule").

The display 600A includes a listing of individual phrases which occur based on different pathology groups 630 and anatomy 640. The display 600A shows the result of sorting by pathology groups 630 (with sorting resulting in groupings of different phrases by surgical changes, malignant or indeterminate tumor, or benign tumor). It will be understood that sorting may also be performed on the display 600A based on phrase 620, anatomy 640, or other fields. Other features for filtering, sorting, and grouping (e.g., based on custom or pre-set criteria) may also be used.

The display 600B includes a more detailed listing of individual phrases which occur based on different pathology groups 630 and anatomy 640, but with the addition of columns to display examination/report date 615, and a text paragraph 650 that includes the phrases. A sorting or grouping of multiple phrases in such a display may be based on date (e.g., recency), importance (e.g., criticality), anatomical areas or body systems, etc.

The displays 600A, 600B each include a link 612 to the particular radiology report which includes the individual phrase. The display 600A also includes a link 614 to one or more radiology images which are referenced by the individual phrase. It will be understood that additional display techniques may be used to highlight, annotate, flag, or identify particular words, areas, or features when such links are selected by an end user.

Figure 7:
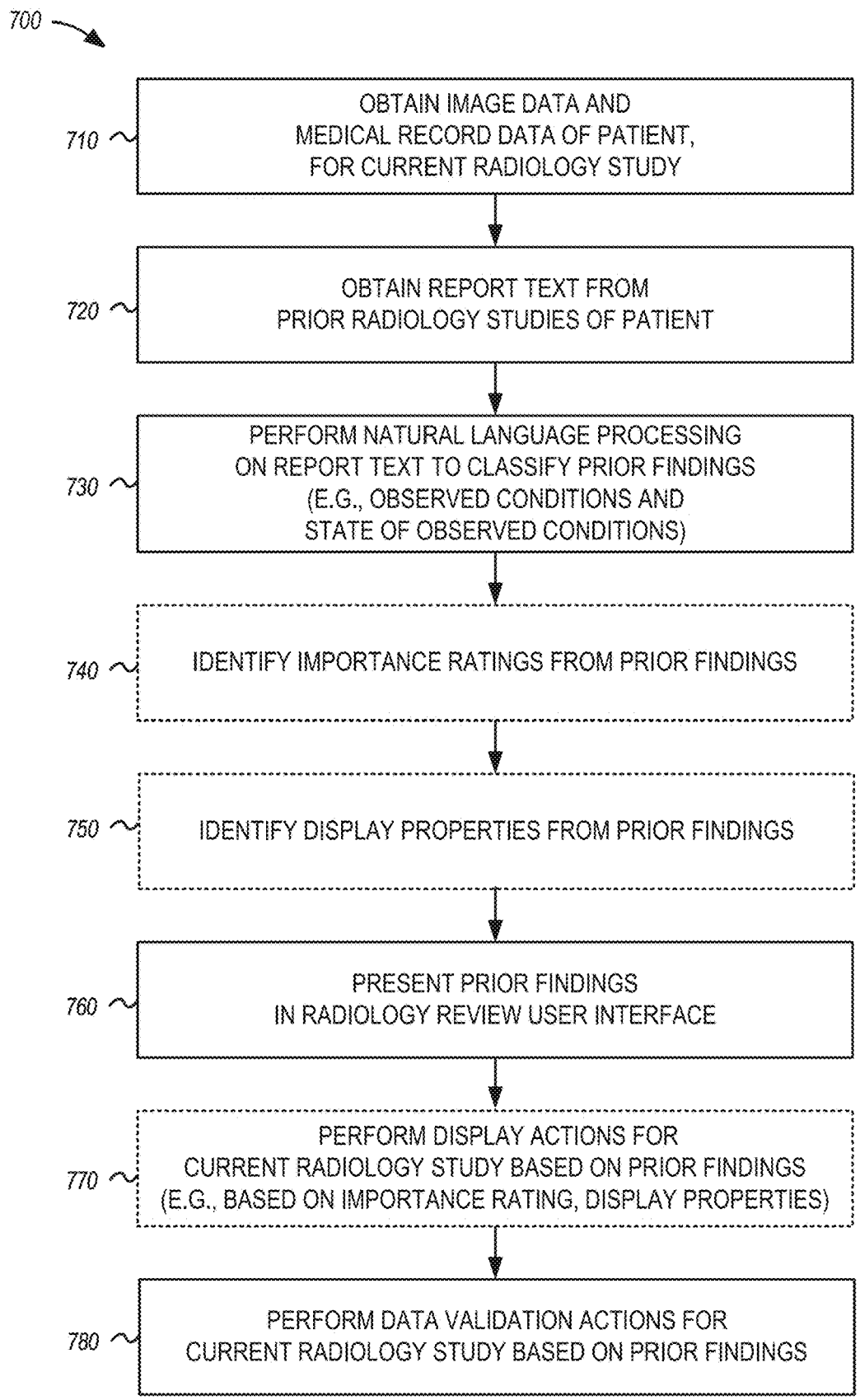
FIG. 7 illustrates a flowchart of a method for prior findings data in a radiology review workflow, according to an example.

FIG. 7 illustrates a flowchart of an example method for processing prior findings data in a radiology review workflow. These operations may be performed at or among the data processing systems depicted in FIGS. 1 and 2, for implementing the NLP processing and display operations depicted in FIGS. 3A to 5.

The flowchart 700 specifically provides examples of operations that can be used to identify, classify, and present prior findings data, based on natural language processing (NLP) of unstructured radiology report text. The following operations include identifying and using such prior findings at the same time as receipt of a new radiology study (referred to as a "current" radiology study in the following paragraphs). However, as noted above, the identification and classification of prior findings from a prior radiology study may occur at a much earlier time, and data for such prior findings may be saved or persisted for use at a later time.

At operation 710, image data and medical record data is obtained (e.g., received), for a patient of a current (new) radiology study. This current radiology study may be evaluated by a radiologist in a radiology review user interface, consistent with the examples above. For instance, the radiology review user interface may display the imaging data and the medical record data for the current radiology study, to allow a radiologist to determine or assess a current medical condition. This user interface may provide at least one text input to receive or select text from the radiologist, to generate a new radiology report for the current radiology study.

At operation 720, report text is obtained (e.g., received or extracted) from one or more prior radiology reports. Such prior radiology reports are prepared for the patient in corresponding prior radiology studies, which may occur at any number of dates, or from any number of medical imaging procedures.

At operation 730, natural language processing is performed on report text to classify one or more prior findings in the prior radiology reports. Such classification may include identifying observed conditions and characteristics of the observed conditions. Such observed conditions may correspond to the use of pathology phrases from prior radiology reports, which involve one or more words to describe a pathology or existence of a respective medical condition, as discussed above. The characteristics of the observed conditions may include features which measure or quantify the condition, such as characteristics that relate to at least one of: size; change; growth; acuity; confidence; negation; limitation; characterization; points of reference based on location or anatomy; laterality; etc. Other types of characteristics (e.g., attributes, properties, conditions, states) may also be identified.

In an example, the natural language processing is implemented by a NLP engine that is trained to classify the prior findings from unstructured text used in radiology reports (e.g., from other patients or training data). For instance, the NLP engine may be trained using pathology phrases, with such pathology phrases providing one or more words to describe a pathology or existence of a respective medical condition, as discussed above. Also, the NLP engine may be trained using attribute words, with such attribute words provided by one or more words that describe a characteristic of a respective medical condition. Other aspects of NLP engine training or operation are discussed above.

At operation 740, one or more importance ratings are optionally identified or determined from conditions identified in the prior findings. The importance ratings may be identified or determined based on a type of the at least one observed condition and the characteristic of the at least one observed condition, from the prior findings. The presentation of the prior findings (at operation 760) may be based on this importance rating (e.g., to exclude or hide prior findings that are irrelevant or of a lesser importance).

At operation 750, one or more display properties are optionally identified or determined from the prior findings. Such display properties may include a sorting or filtering property for the conditions identified in the prior findings. For instance, such display properties may be used in a scenario where the at least one sorting or filtering property relates to an anatomical area, pathology, date, or phrasing of the at least one observed condition.

At operation 760, actions are performed at the radiology review user interface (or, at systems connected to this user interface) to present the prior findings (e.g., in a display provided by the user interface, or in the communication of data to a computer system with a user interface). For instance, such presentation may include an implementation of the sorting, filtering, or grouping features discussed above. In a further example, such a presentation occurs with the use of prior findings which are assigned into a plurality of pathology groups. Such pathology groups may be associated with particular pathology phrases used in the prior radiology reports. The presentation of prior findings in the radiology review user interface then may be filtered, sorted, or grouped based on these plurality of pathology groups.

In a specific example, presenting of the prior findings includes a display of a condensed view of the prior findings in the radiology review user interface, such as is shown in FIG. 6A. This may include the output of at least: an identification of a pathology phrase for each of the at least one observed condition; an identification of an anatomical area for each of the at least one observed condition; and a categorization of a pathology group associated with the pathology phrase and the anatomical area for each of the at least one observed condition. In another specific example, presenting of the prior findings includes a display of a detailed view of the prior findings in the radiology review user interface, such as is shown in FIG. 6B. This may include the features of the condensed view, in addition to: an identification of a date of the prior findings; and an identification of text from the prior radiology report for each of the at least one observed condition.

At operation 770, additional display actions may be optionally performed with the current radiology study based on the prior findings. This may include the implementation of additional filtering, sorting, or grouping functions, in automated or user-implemented forms. In a specific example, the prior findings are linked in the radiology review user interface to text, images, or medical data from the corresponding prior radiology study. This allows the interactive comparison of prior findings and additional images or data for such prior findings.

At operation 780, data validation actions may be performed for a current radiology study, based on prior findings. For example, text that is entered or composed by a radiologist for a new radiology report may be validated, to ensure consistency or accuracy. Likewise, clearly incorrect medical conditions or attributes may be identified or flagged to a radiologist based on conditions that would be expected due to the prior findings.

Figure 8:
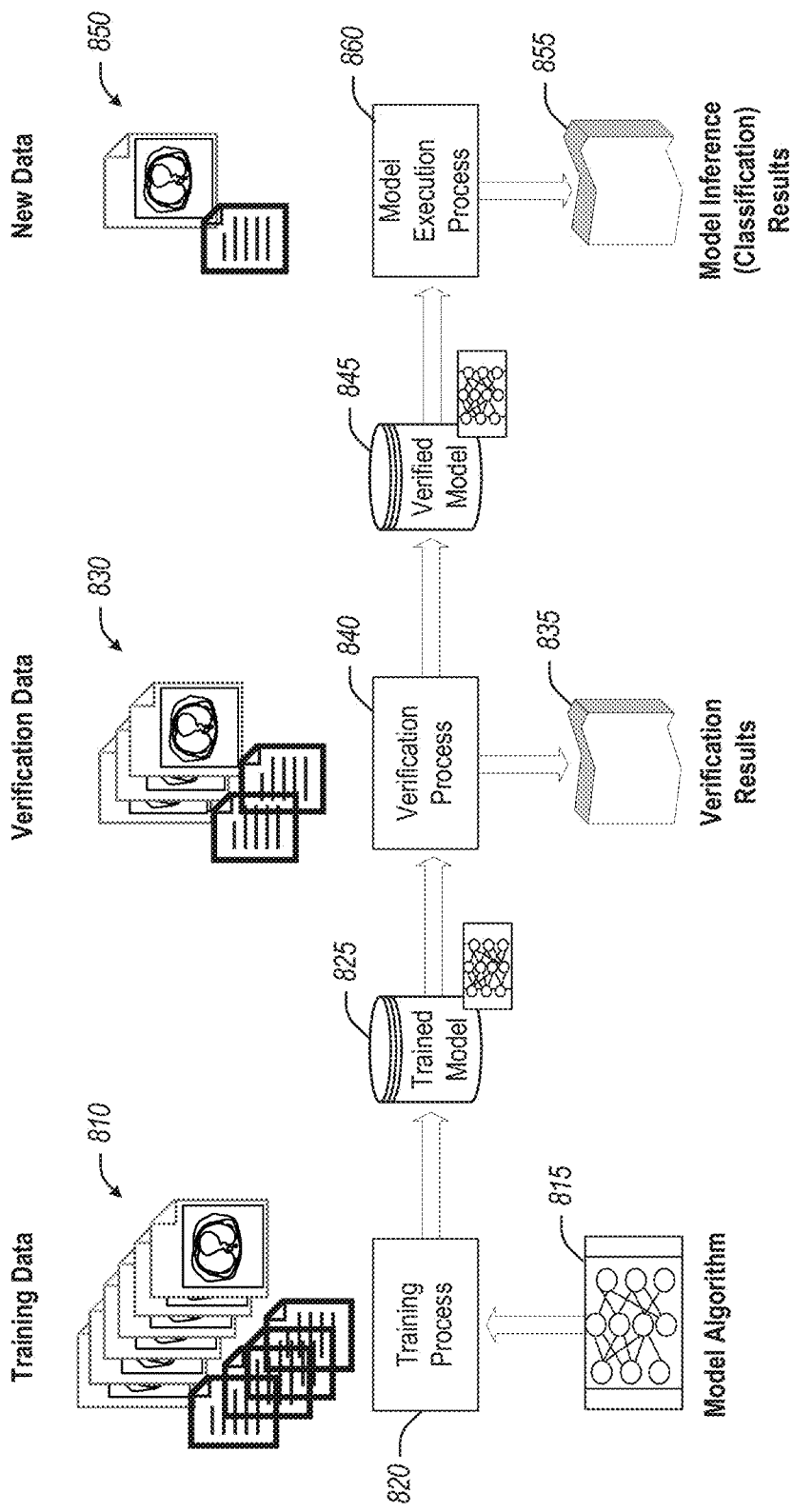
FIG. 8 illustrates an example trained model deployment use case, according to an example.

FIG. 8 illustrates an example arrangement of a system that can be used to train, validate, and operate an AI model, such as an AI model to classify data, generate inferences, perform regression, produce predictions or labels, or otherwise produce outputs from a data input. It will be understood that the NLP processing engine discussed above may be implemented with use of one or more AI models.

As shown, a trained AI model 825 may be produced from a training process 820. This training process may receive a set of classified training data 810 which is provided as input to the training process, to operate on a model algorithm 815 to adjust the weights, values, or properties used within the model algorithm as part of a learning procedure. This model algorithm 815 may include any of the types of AI algorithms, engines, or arrangements discussed herein, and involve unsupervised, supervised, or reinforcement learning approaches as part of training operations. In an example, the classified training data 810 may include or be derived from image data, text data, data values, or some combination thereof.

The trained model 825 is provided to a verification process 840, which produces verification results 835 from a set of verification data 830. For instance, the verification process may use a process to ensure compliance of a trained model with some specification or approach. It will be understood that other forms of evaluation and verification, reinforcement, and adaptive learning may also be performed with use of the verification results 835.

Upon completion of the verification process, the trained model 825 is now identified as a verified model 845, for use within a model execution process 860. The model execution process 860 is used to operate the AI model upon a set of new data 850, such as data obtained for a subject (e.g., patient) with a medical imaging procedure (e.g., imaging data, text data, metadata), as discussed above. In an example, such "new" data may include historical data (e.g., from prior radiology studies) which is newly analyzed but captured at an earlier time. The model execution process 860 is used to produce model inference results 855, which may constitute a number of forms, such as classifications, labels, values, annotations, identified pixels, generative data, etc.

Figure 9:
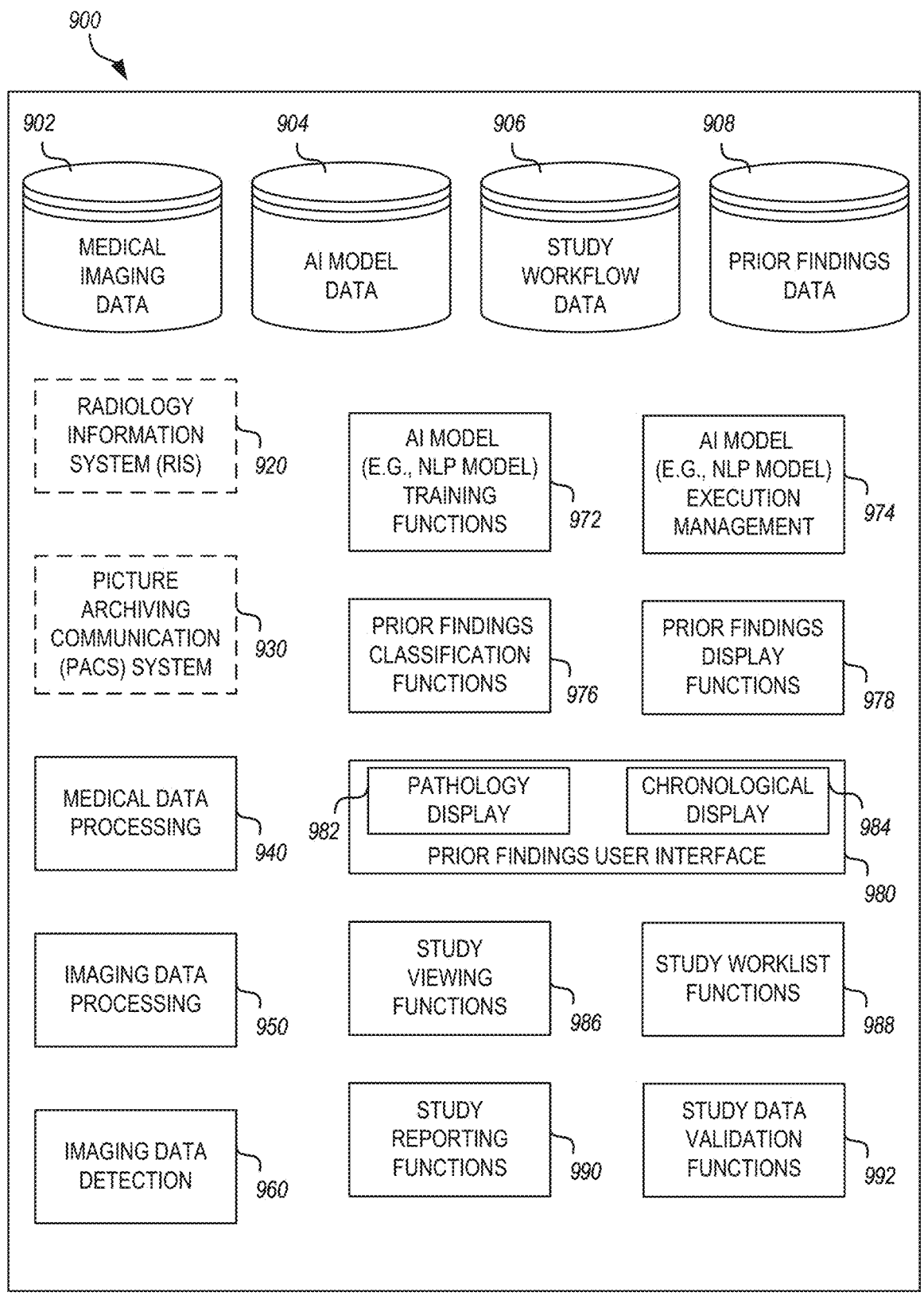
FIG. 9 illustrates a configuration of a computing system arranged to process medical imaging data and associated radiology report data, according to an example.

FIG. 9 illustrates an example configuration of a system architecture 900 configured to implement a processing system with functionality according to the examples described herein. System architecture 900 may implement features of the workflow processing system 102, the image evaluation system 106, the data processing system 108, the radiology report data processing system 220, the medical imaging evaluation system 260, or the like.

The system architecture 900 includes features of a radiology information system (RIS) 920 a picture archiving communication system (PACS) 930 (with RIS 920 and PACS 930 optionally implemented in the architecture 900 or in external systems), medical data processing 940, image data processing 950, and image data detection 960. Specific functions for prior findings may be implemented by AI model (or algorithm) training functions 972, AI model (or algorithm) execution management 974, prior findings classification functions 976, and prior findings display functions 978. These and other functions may be embodied by any number of software or hardware forms (including through the use of physical or logical blocks of computer instructions, which may, for instance, be organized as an object, procedure, or function).

The system architecture 900 also includes a prior findings user interface 980 configured to provide a pathology-based display 982 (e.g., primarily filtered or sorted based on particular pathologies or medical conditions that are identified in prior reports, such as is depicted in FIG. 6A), or a chronological-based display 984 (e.g., primarily filtered or sorted based on the date of identification of a condition status in a prior report, such as is depicted in FIG. 6B). Other displays may also be provided consistent with the examples above.

The system architecture 900 also includes additional functions for the management and display of radiology studies, such as study viewing functions 986, study worklist functions 988, study reporting functions 990, or study data validating functions 992. More detail of the use cases for the generation and preparation of radiology reports is provided with reference to FIGS. 1 and 2, above.

In operation with these features, the system architecture 900 includes a plurality of databases or data stores, including a medical imaging database 902, an AI model database 904, a study workflow database 906, and a study workflow database 908. The medical imaging database 902 may provide a location for storage of imaging data (and metadata) for medical imaging procedures and associated studies. The machine learning model database 904 may provide a location for storage of AI models or algorithms, inputs, and relevant parameters for operation of such models or algorithms. The study workflow database 906 may provide a location for storage of workflow states of particular studies, preferences for workflow operations, and other data fields used to assist any number of radiology read workflow operations. The prior findings database 908 may provide a location for storage of information for prior findings (e.g., indexed or evaluated at an earlier time), preferences for display or presentation of prior findings, and other data fields used to assist the analysis or output of prior findings.

The respective features of the system architecture 900 may perform functional operations to affect the prior findings identification, image and text processing, and radiology study management techniques described herein. For example, the RIS 920 may be used to provide respective information processing functions of a Radiology Information System (RIS). The PACS 930 may be used to provide image storage and access features of a Picture Archiving Communication System (PACS). The medical data processing 940 may be used to process medical data (including radiology orders), and determine patient information relevant to a new (or, historical) patient radiology. The image data processing 950 may be used to coordinate or perform imaging processing operations on imaging data obtained from a set of data associated with a medical imaging procedure, or from a customer imaging device, an image archive, medical facility data store, or other imaging data source. The image data detection 960 may be used to implement specific AI models, such as with performance of a trained machine learning or deep learning model to detect certain medical conditions within the radiology images.

The AI model training functions 972 may be used to implement training of an AI model or algorithm (e.g., a model to implement an NLP engine), such as with the use of imaging and non-imaging data completed by previous study evaluations. The AI model execution management 974 may be used to execute or invoke AI models within specific data analysis or processing workflows, as discussed above. The prior findings classification functions 976 may be used to perform analysis and classification on the text content from current or historical radiology reports, as discussed above. The prior findings display functions 978 may be used to control or modify the display of the prior finding classifications (e.g., pathologies, phrases, and other medical conditions), as discussed above.

The study viewing functions 986 may be used to view studies (and specific types of rendering data) on screen by an evaluating user, which may be influenced by the detection of certain medical conditions, prioritization, or results of the image detection operations and the workflows. The study worklist functions 988 may be used to receive assignments to one or more evaluators (and to facilitate the transfer of data to computing systems associated with the one or more evaluators) based on prior findings, image detection operations, or related workflows. The study reporting functions 990 may be used to assist the creation of radiology report(s) by the evaluating user, and the content of such reports may be influenced or assisted by the results of the prior findings or the additional processing discussed herein. The study data validation functions 992 may be used to verify data entry (e.g., specific findings, measurements) or other data from current or prior radiology studies. Additional functions and components, not shown in FIG. 9, may be provided to implement the data processing provided within the NLP engine, the workflow assignment and management features, and data classification or extraction features discussed above.

Figure 10:
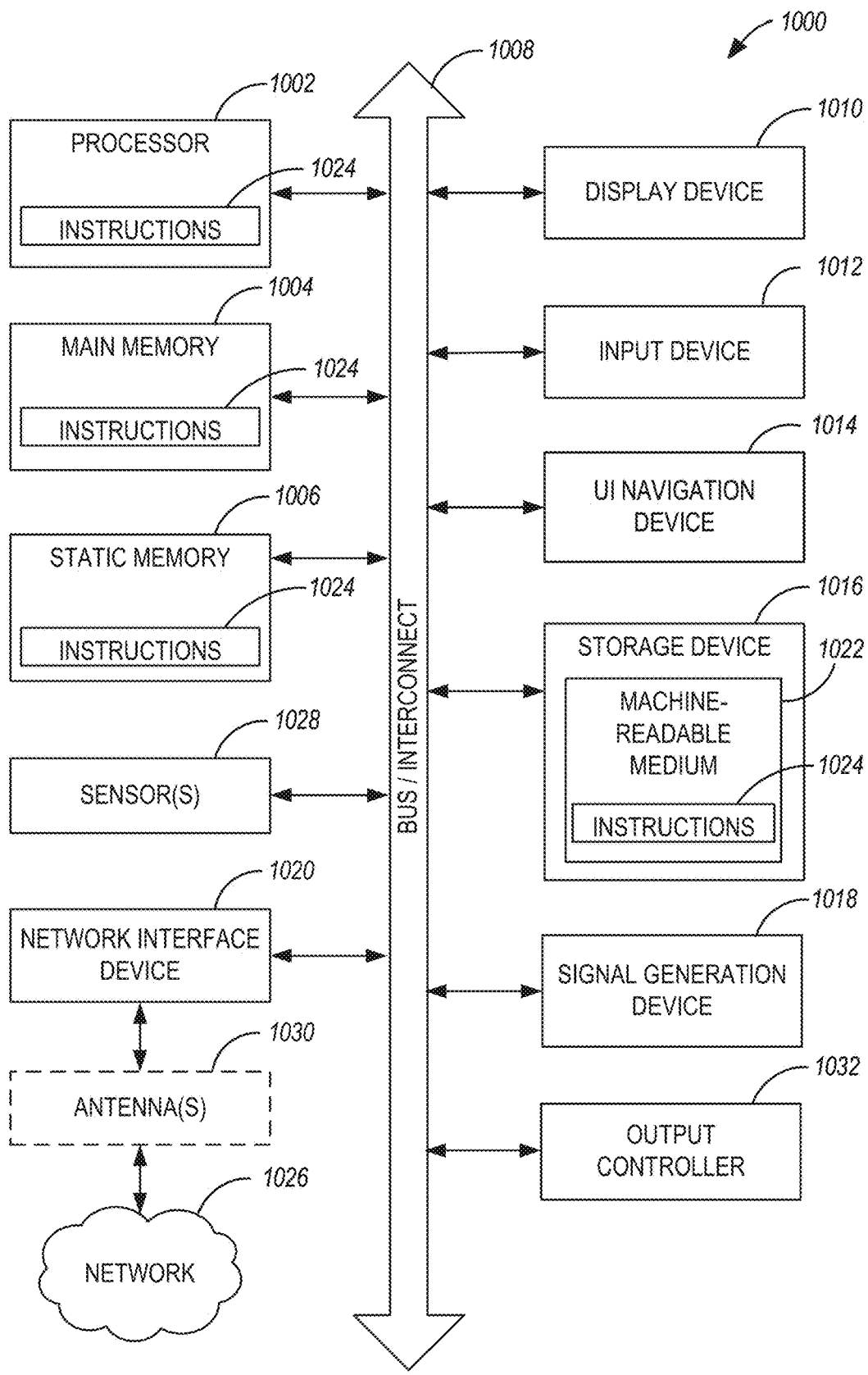
FIG. 10 illustrates an example of a machine configured to perform computing operations, according to an example.

FIG. 10 is a block diagram illustrating an example computing system 1000 upon which any one or more of the methodologies herein discussed may be run according to an example described herein. Computer system 1000 may be embodied as a computing device, providing operations of the components featured in the various figures, including components of the workflow processing system 102, the image capture system 104, the image evaluation system 106, the data processing system 108, components and data storage elements in system architecture 900, or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1000 includes a processor 1002 (e.g., a central processing unit (CPU), a graphics processing unit (GPU) or both), a main memory 1004 and a static memory 1006, which communicate with each other via an interconnect 1008 (e.g., a link, a bus, etc.). The computer system 1000 may further include a video display unit 1010, an alphanumeric input device 1012 (e.g., a keyboard), and a user interface (UI) navigation device 1014 (e.g., a mouse). In one embodiment, the video display unit 1010, input device 1012 and UI navigation device 1014 are a touch screen display. The computer system 1000 may additionally include a storage device 1016 (e.g., a drive unit), a signal generation device 1018 (e.g., a speaker), an output controller 1032, and a network interface device 1020 (which may include or operably communicate with one or more antennas 1030, transceivers, or other wireless communications hardware), and one or more sensors 1028.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the computer system 1000, with the main memory 1004, static memory 1006, and the processor 1002 constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions 1024. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of non-transitory machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks, and CD-ROM and DVD-ROM disks.

The instructions 1024 may further be transmitted or received over a communications network 1026 using a transmission medium via the network interface device 1020 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the features in the system architecture 900 of the processing system may be client-operated software or be embodied on a server at a cloud, edge, or intermediate location, running an operating system with software, virtual machines, containers, or the like running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, features, or mechanisms. Such items are tangible entities (e.g., hardware) capable of performing specified operations and may be configured or arranged in a certain manner. In an example, circuits may be arranged (e.g., internally or with respect to external entities such as other circuits) in a specified manner as a module, component, or feature. In an example, the whole or part of one or more computer systems (e.g., a standalone, client or server computer system) or one or more hardware processors may be configured by firmware or software (e.g., instructions, an application portion, or an application) as an item that operates to perform specified operations. In an example, the software may reside on a machine readable medium. In an example, the software, when executed by underlying hardware, causes the hardware to perform the specified operations.

Accordingly, such modules, components, and features are understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules, components, and features are temporarily configured, each of the items need not be instantiated at any one moment in time. For example, where the modules, components, and features comprise a general-purpose hardware processor configured using software, the general-purpose hardware processor may be configured as respective different items at different times. Software may accordingly configure a hardware processor, for example, to constitute a particular item at one instance of time and to constitute a different item at a different instance of time.

Additional examples of the presently described method, system, and device embodiments are suggested according to the structures and techniques described herein. Other non-limiting examples may be configured to operate separately, or can be combined in any permutation or combination with any one or more of the other examples provided above or throughout the present disclosure.

What is claimed is:

1. A method of processing prior findings data in a radiology review workflow, performed with electronic operations executed with a processor of a computing device, the electronic operations comprising:
   receiving unstructured text from a prior radiology report of a patient, the prior radiology report prepared for the patient in a corresponding prior radiology study;
   processing the unstructured text with a natural language processing (NLP) engine to classify prior findings in the prior radiology study, each of the prior findings indicating at least one observed condition and a characteristic of the at least one observed condition,
   wherein the NLP engine includes a neural network that is pre-trained to classify the prior findings, wherein the neural network is pre-trained by associating patterns and words from unstructured text used in training radiology reports with training pathology phrases, and
   wherein the neural network operates to classify the prior findings in the prior radiology study of the patient by:
      parsing the unstructured text from the prior radiology report to identify pathology phrases that describe a pathology or existence of a respective medical condition; and
      determining the at least one observed condition and the characteristic of the at least one observed condition from textual usage of the identified pathology phrases; and
   presenting the prior findings in a radiology review user interface, the radiology review user interface to display the at least one observed condition and the characteristic of the at least one observed condition that is indicated by the prior radiology report.

2. The method of claim 1, the electronic operations further comprising:
   identifying an importance rating for the at least one observed condition, based on at least one of: a type of the at least one observed condition, the characteristic of the at least one observed condition, or an anatomy of a current radiology study undergoing interpretation in the radiology review user interface;
   wherein the presenting of the prior findings is based on the importance rating for each of the at least one observed condition.

3. The method of claim 1, the electronic operations further comprising:
   identifying at least one sorting or filtering property for the at least one observed condition, wherein the at least one sorting or filtering property relates to an anatomical area, pathology, date, or phrasing of the at least one observed condition;
   wherein the presenting of the prior findings is based on the at least one sorting or filtering property for the at least one observed condition.

4. The method of claim 1, wherein each of the training pathology phrases used for training the neural network comprises one or more words that describe a pathology or existence of a respective medical condition, and wherein the training of the neural network comprises use of supervised learning or unsupervised learning to associate the patterns and words arranged in the unstructured text with the training pathology phrases.

5. The method of claim 1, the electronic operations further comprising:
   assigning the prior findings into a plurality of pathology groups, wherein the plurality of pathology groups are associated with the pathology phrases used in the prior radiology report;
   wherein a display provided by the presenting of the prior findings in the radiology review user interface is filtered, sorted, or grouped based on the plurality of pathology groups.

6. The method of claim 1, wherein the presenting of the prior findings includes a display of a condensed view of the prior findings in the radiology review user interface, the condensed view including at least:
   an identification of a pathology phrase for each of the at least one observed condition;
   an identification of an anatomical area for each of the at least one observed condition; and
   a categorization of a pathology group associated with the pathology phrase and the anatomical area for each of the at least one observed condition.

7. The method of claim 1, wherein the presenting of the prior findings includes a display of a detailed view of the prior findings in the radiology review user interface, the detailed view including at least:
   an identification of a date of the prior findings;
   an identification of a pathology phrase for each of the at least one observed condition;
   an identification of an anatomical area for each of the at least one observed condition;
   a categorization of a pathology group associated with the pathology phrase and the anatomical area for each of the at least one observed condition; and an identification of text from the prior radiology report for each of the at least one observed condition.

8. The method of claim 4, wherein the training of the neural network further comprises use of attribute words, and wherein each of the attribute words comprises one or more words to describe a characteristic of a respective medical condition.

9. The method of claim 1, wherein the characteristic of the at least one observed condition relates to at least one of: size; change; growth; acuity; confidence; negation; limitation; characterization; points of reference based on location or anatomy; or laterality.

10. The method of claim 1, wherein the prior findings are linked in the radiology review user interface to text, images, or medical data from the corresponding prior radiology study.

11. The method of claim 1, the electronic operations further comprising:
   selecting a portion of the prior findings to be presented in the radiology review user interface, based on at least one current medical condition associated with a current radiology study undergoing interpretation in the radiology review user interface.

12. The method of claim 11, wherein the current radiology study includes imaging data and medical record data, the electronic operations further comprising:
   receiving the imaging data for the current radiology study;
   receiving the medical record data associated with the patient; and
   identifying the at least one current medical condition based on analysis of the imaging data and the medical record data.

13. The method of claim 12, wherein the radiology review user interface displays the imaging data and the medical record data for the current radiology study, and wherein the radiology review user interface includes at least one text input to receive or select text for a new radiology report of the current radiology study.

14. The method of claim 13, the electronic operations further comprising:
   validating the text for the new radiology report, based on the prior findings.

15. The method of claim 13, wherein the imaging data includes medical images provided from a radiological imaging procedure, wherein the medical record data includes data provided from a radiological imaging order, and wherein the current radiology study corresponds to a request for diagnostic evaluation of the medical images as indicated by the radiological imaging order.

16. A non-transitory machine-readable storage medium, the machine-readable storage medium comprising instructions that, when executed by a processor of a computing device, causes the computing device to perform operations comprising:
   identifying unstructured text from a prior radiology report of a patient, the prior radiology report prepared for the patient in a corresponding prior radiology study;
   processing the unstructured text with a natural language processing (NLP) engine to classify prior findings in the prior radiology study, each of the prior findings indicating at least one observed condition and a characteristic of the at least one observed condition,
   wherein the NLP engine includes a neural network that is pre-trained to classify the prior findings, wherein the neural network is pre-trained by associating patterns and words from unstructured text used in training radiology reports with training pathology phrases, and wherein the neural network is configured to classify the prior findings in the prior radiology study of the patient by:
      parsing the unstructured text from the prior radiology report to identify pathology phrases that describe a pathology or existence of a respective medical condition; and
      determining the at least one observed condition and the characteristic of the at least one observed condition from textual usage of the identified pathology phrases; and
   communicating the prior findings for display in a radiology review user interface, the radiology review user interface to display the at least one observed condition and the characteristic of the at least one observed condition that is indicated by the prior radiology report.

17. The machine-readable storage medium of claim 16, the instructions further to cause the computing device to perform operations comprising:
   identifying an importance rating for the at least one observed condition, based on at least one of: a type of the at least one observed condition, the characteristic of the at least one observed condition, or an anatomy of a current radiology study undergoing interpretation in the radiology review user interface; and
   identifying at least one sorting or filtering property for the at least one observed condition, wherein the at least one sorting or filtering property relates to an anatomical area, pathology, date, or phrasing of the at least one observed condition;
   wherein the display of the prior findings in the radiology review user interface is based on the importance rating or the at least one sorting and filtering property for each of the at least one observed condition.

18. The machine-readable storage medium of claim 16, the instructions further to cause the computing device to perform operations comprising:
   assigning the prior findings into a plurality of pathology groups, wherein the plurality of pathology groups are associated with particular pathology phrases used in the prior radiology report;
   wherein the display of the prior findings in the radiology review user interface is filtered, sorted, or grouped based on the plurality of pathology groups.

19. The machine-readable storage medium of claim 16, wherein the characteristic of the at least one observed condition relates to at least one of: size; change; growth; acuity; confidence; negation; limitation; characterization; points of reference based on location or anatomy; or laterality.

20. The machine-readable storage medium of claim 16, wherein each of the training pathology phrases used for training the neural network comprises one or more words that describe a pathology or existence of a respective medical condition;
   wherein the training of the neural network comprises use of supervised learning or unsupervised learning to associate the patterns and words arranged in the unstructured text with the training pathology phrases; and
   wherein the training of the neural network further comprises use of attribute words, and wherein each of the attribute words comprises one or more words to describe a characteristic of a respective medical condition.

21. A computing system, comprising:
a processor; and
a memory device comprising instructions stored thereon, which when executed by the processor, configure the processor to perform electronic operations with the computing system comprising:
obtaining unstructured text from a prior radiology report of a patient, the prior radiology report prepared for the patient in a corresponding prior radiology study;
processing the unstructured text with a natural language processing (NLP) engine to classify prior findings in the prior radiology study, each of the prior findings indicating at least one observed condition and a characteristic of the at least one observed condition,
wherein the NLP engine includes a neural network that is pre-trained to classify the prior findings, wherein the neural network is pre-trained by associating patterns and words from unstructured text used in training radiology reports with training pathology phrases, and
wherein the neural network operates to classify the prior findings in the prior radiology study of the patient by:
parsing the unstructured text from the prior radiology report to identify pathology phrases that describe a pathology or existence of a respective medical condition; and
determining the at least one observed condition and the characteristic of the at least one observed condition from textual usage of the identified pathology phrases; and
outputting the prior findings for use in a radiology review user interface, the radiology review user interface to display the at least one observed condition and the characteristic of the at least one observed condition that is indicated by the prior radiology report.

22. The computing system of claim 21, the instructions further to configure the processor to perform electronic operations comprising:
identifying an importance rating for the at least one observed condition, based on at least one of: a type of the at least one observed condition, the characteristic of the at least one observed condition, or an anatomy of a current radiology study undergoing interpretation in the radiology review user interface; and
identifying at least one sorting or filtering property for the at least one observed condition, wherein the at least one sorting or filtering property relates to an anatomical area, pathology, date, or phrasing of the at least one observed condition;
wherein the display of the prior findings in the radiology review user interface is based on the importance rating or the at least one sorting and filtering property for each of the at least one observed condition.

23. The computing system of claim 21, the instructions further to configure the processor to perform electronic operations comprising:
assigning the prior findings into a plurality of pathology groups, wherein the plurality of pathology groups are associated with particular pathology phrases used in the prior radiology report;
wherein the display of the prior findings in the radiology review user interface is filtered, sorted, or grouped based on the plurality of pathology groups.

24. The computing system of claim 21, wherein the characteristic of the at least one observed condition relates to at least one of: size; change; growth; acuity; confidence; negation;
limitation; characterization; points of reference based on location or anatomy; or laterality.

25. The computing system of claim 23, wherein each of the training pathology phrases used for training the neural network comprises one or more words that describe a pathology or existence of a respective medical condition;
wherein the training of the neural network comprises use of supervised learning or unsupervised learning to associate the patterns and words arranged in the unstructured text with training pathology phrases; and
wherein the training of the neural network further comprises use of attribute words, and wherein each of the attribute words comprises one or more words to describe a characteristic of a respective medical condition.

* * * * *